US007662389B2

(12) United States Patent
Clark et al.

(10) Patent No.: US 7,662,389 B2
(45) Date of Patent: Feb. 16, 2010

(54) USE OF SERUM AMYLOID A GENE IN DIAGNOSIS AND TREATMENT OF GLAUCOMA AND IDENTIFICATION OF ANTI-GLAUCOMA AGENTS

(75) Inventors: Abbot F. Clark, Arlington, TX (US); Wan-Heng Wang, Grapevine, TX (US); Loretta Graves McNatt, Hurst, TX (US)

(73) Assignee: Alcon, Inc., Hunenberg (CH)

( * ) Notice: Subject to any disclaimer, the term of this patent is extended or adjusted under 35 U.S.C. 154(b) by 130 days.

(21) Appl. No.: 11/615,454

(22) Filed: Dec. 22, 2006

(65) Prior Publication Data
US 2007/0208043 A1 Sep. 6, 2007

Related U.S. Application Data

(63) Continuation-in-part of application No. 11/000,757, filed on Dec. 1, 2004, now Pat. No. 7,357,931.

(51) Int. Cl.
*A61K 39/00* (2006.01)
(52) U.S. Cl. ........................................ 424/184.1; 514/2
(58) Field of Classification Search ........................ None
See application file for complete search history.

(56) References Cited

U.S. PATENT DOCUMENTS

| 4,656,127 | A | 4/1987 | Mundy |
| 4,998,617 | A | 3/1991 | Ladd, Jr. et al. |
| 5,459,039 | A | 10/1995 | Modrich et al. |
| 5,545,628 | A | 8/1996 | Deboeck et al. |
| 5,593,826 | A | 1/1997 | Fung et al. |
| 6,433,018 | B1 | 8/2002 | Siddiqui et al. |
| 7,357,931 | B2 | 4/2008 | Clark et al. |
| 2002/0102581 | A1 | 8/2002 | Hageman et al. |
| 2003/0078274 | A1* | 4/2003 | Lipton ........................ 514/256 |

FOREIGN PATENT DOCUMENTS

| EP | 1 196 167 B | 4/2006 |
| FR | 2650840 | 8/1989 |
| WO | WO 91/02087 A1 | 2/1991 |
| WO | WO 92/15712 A1 | 9/1992 |
| WO | WO 94/16101 A2 | 7/1994 |
| WO | WO 94/16101 A3 | 7/1994 |
| WO | WO 2005/060542 A2 | 7/2005 |
| WO | WO 2005/060542 A3 | 7/2005 |

OTHER PUBLICATIONS

Barany, Proc. Natl. Acad. Sci. USA 88:189-193 (1991); "Genetic disease detection and DNA amplification using cloned thermostable ligase".
Bengtsson, "Incidence of manifest glaucoma," Br J Ophthalmol, vol. 73, pp. 483-487 (1989).
Cotton et al., Proc. Natl. Acad. Sci. USA 85:4397 (1988); "Reactivity of cytosine and thymine in single-base-pair mismatches with hydroxylamine and osmium tetroxide and its application to the study of mutations".
Cotton, Mutat. Res. 285:125-144 (1993); "Current methods of mutation detection".
Cronin et al. , Human Mutation 7:244-255 (1996); "Cystic Fibrosis Mutation Detection by Hybridization to Light-Generated DNA Probe Arrays".
Ermilov et al. (1993); Arkh Patol.; "Senile amyloidosis of the eye as a manifestation of senile cerebral amyloidosis" [abstract] with article in Russian 55(6):43-45.
Furlenato, CJ, and Campa A, Biochem. Biophys. Res. Commun 268:405-408 (2002), "A novel function of serum amyloid A: a potent stimulus for the release of tumor necrosis factor-alpha, interleukin-1 beta, and interleukin-8 by human blood neutrophil".
Gasparini et al. , Mol. Cell Probes 6:1-7 (1992); "Restriction site generating-polymerase chain reaction (RG-PCR) for the probeless detection of hidden genetic variation: application to the study of some common cystic fibrosis mutations".
Gibbs et al., Nucleic Acids Res. 17:2437-2448 (1989); "Detection of single DNA base differences by competitive oligonucleotide priming".
Griffin et al., Appl. Biochem Biotechnol. 38:147-159 (1993); "DNA Sequencing Recent Innovations and Future Trends".
Guatelli, J. C., et al., Proc. Natl. Acad. Sci. USA 87:1874-1878 (1990); "Isothermal, in vitro amplification of nucleic acids by a multienzyme reaction modeled after retroviral replication".
Hagihara K et al, 2004, Biochemical and Biophysical Research Communications, "IL-6 plays a critical role in the synergistic induction of human serum Amyloid A (SAA) gene when stimulated with proinflammatory cytokines as analysed with an SAA isoform real-time quantitative RT-PCR assay system", 314, 363-369.
Hayashi, Genet. Anal. Tech. Appl. 9:73-79 (1992); "PCR-SSCP: A Method for Detection of Mutations".
He, R, Sang H, Ye, RD, Serum Amyloid A induces IL-8 secretion through a G protein-coupled receptor, FPRL1/LXA4R, Blood 101:1572-1581 (2003).
Hsu et al., Carcinogenesis 15:1657-1662(1994); "Detection of DNA point mutations with DNA mismatch repair enzymes".
Krasnov et al. (Jan.-Mar. 1996); Vestn Oftalmol, "Morphological features of senile and secondary amyloidosis of the iris and sclera in patients with glaucoma" [abstract] with article will be in Russian 12(1):24-6.
Kumon, Y. et al, Acute-phase, but not constitutive serum amyloid A (SAA) is chemotactic for cultured human aortic smooth muscle cells, AMYLOID 9:237-241 (2002a).
Kumon Y. et al., Transcriptional regulation of Serum Amyloid A1 gene expression in human aortic smooth muscle cells involves CCAAT/enhancer binding proteins (C/EBP) and is distinct from HepG2 cells,, Scand. J. Immunol. 56:504-511 (2002b).
Kumon, Y. et al., Dexamethasone, but not IL-1 alone, upregulates acute-phase serum amyloid A gene expression and production by cultured human aortic smooth muscle cells, Scand J. Immunol. 53:7-12 (2001).

(Continued)

*Primary Examiner*—Anand U Desai
(74) *Attorney, Agent, or Firm*—Teresa J. Schultz

(57) ABSTRACT

The present invention provides compositions and methods for treating glaucoma, methods for diagnosing glaucoma, and methods for identifying agents which may be useful in the treatment of glaucoma. More specifically, the present invention describes the use of agents that modulate the expression of serum amyloid A.

2 Claims, 14 Drawing Sheets

OTHER PUBLICATIONS

Kuppuswamy, M. N. et al. Proc. Natl. Acad. Sci. (U.S.A.) 88:1143-1147 (1991); "Single nucleotide primer extension to detect genetic diseases: Experimental application to hemophilia B (factor IX) and cystic fibrosis genes".

Kwoh, D. Y., et al., Proc. Natl. Acad. Sci. USA 86:1173-1177 (1989); "Transcription-based amplification system and detection of amplified human immunodeficiency virus type 1 with a bead-based sandwich hybridization format".

Landegren, U. et al., Science 241:1077:1080 (1988); "A Ligase-Mediated Gene Detection Technique".

Liang, J.S., Sloane, J.A., Wells, J.M., Abraham, C.R., Fine, R.E., and Sipe, J.D., Evidence for local production of acute phase response apolipoprotein serum amyloid A in Alzheimer's disease brain, Neurosci. Lett. 225:73-76 (1997).

Lizardi, P. M. et al., Bio/Technology 6:1197-1202 (1988); "Exponential Amplification of Recombinant-RNA Hybridization Probes".

Maxam and Gilbert, Proc. Natl. Acad. Sci. USA 74:560 (1977); "A new method for sequencing DNA".

Miida T., Yamada, T., Yamadera, T., Ozaki, K., Inano, K., Okada, M., Serum amyloid A protein generates pre-beta 1 high-density lipoprotein from alpha-migrating high-density lipoprotein, Biochem. 38(51):16958-16962 (1999).

Myers et al., Nature 313:495 (1985a); "Detection of singie base substitutions in total genomic DNA".

Myers et al., Science 230:1242 (1985b); "Detection of Single Base Substitutions by Ribonuclease Cleavage at Mismatches in RNA:DNA Duplexes".

Nickerson, D. A. et al., Proc. Natl. Acad. Sci. USA 87:8923-27 (1990); "Automated DNA diagnostics using an ELISA-based oligonucleotide ligation assay".

O'Hara, R., Murphy, E.P., Whitehead, A.S., FitzGerald, O., and Bresnihan, B., Acute-phase serum amyloid A production by rheumatoid arthritis synovial tissue, Arthritis Res. 2:142-148 (2000).

Orita et al., Proc. Natl. Acad. Sci. USA 86:2766 (1989); "Detection of polymorphisms of human DNA by gel electrophoresis as single-strand conformation polymorphisms".

PCT International Search Report of a related PCT Application No. PCT/US04/40156, mailed Jul. 26, 2006.

Prosser, Tibtech 11:238 (1993): "Detecting single-base mutations".

Roest et al., Hum. Mol. Genet. 2:1717-1721 (1993); "Protein truncation test (PTT) for rapid detection of translation-terminating mutations".

Saiki et al., Nature 324:163-166 (1986); "Analysis of enzymatically amplified •-globin and HLA-DQ• DNA with allele-specific oligonucleotide probes".

Saiki et al., Proc. Natl. Acad. Sci. USA 86:6230-6234 (1989); "Genetic analysis of amplified DNA with immobilized sequence-specific oligonucleotide probes".

Sanger et al. Proc. Natl. Acad. Sci. USA 74:5463 (1977); "DNA sequencing with chain-terminating inhibitors".

Schwartz et al. (1982); Ophthalmology, 89(4):394-401Sokolov, B.P., Nucl. Acids Res. 18:3671 (1990); "Primer extension technique for the detection of single nucleotide in genomic DNA".

Sokolov, B.P., Nucl. Acids Res. 18:3671 (1990); "Primer extension technique for the detection of single nucleotide in genomic DNA".

Strong, N. P., "How optometrists screen for glaucoma: A survey", Ophthal. Physiol. Opt., 12:3-7 (1992).

Syvanen, A. -C., et al., Genomics 8:684-692 (1990); "A Primer-Guided Nucleotide Incorporation Assay in the Genotyping of Apolipoprotein E".

Thorn, C.F. and Whitehead, A.S., Differential glucocorticoid enhancement of the cytokine-driven transcriptional activation of the human actue phase serum amyloid A genes, SAA1 and SAA, J. Immunol. 169:399-406 (2002).

Tobe et al., Nucleic Acids Res. 24:3728-3732 (1996); "Single-well genotyping of diallelic sequence variations by a two-color ELISA-based oligonucleotide ligation assay".

Uhlar C et al., 1997, "Use of the acute phase serum anyloid A2 (SAA2) gene promoter in the analysis of pro-and anti-inflammatory mediators: differential kinetics of SAA2 promoter induction by IL-1 beta and TNF-alpha compared to IL06", Journal of Immunological Methods, 203, 123-130, especially Abstract.

Uhlar, C.M., and Whitehead, A.S., Serum amyloid A, the major vertebrate acute-phase reactant, Eur. J. Biochem. 265:501-523 (1999).

Urleli-Shoval, S., Cohen, P., Eisenberg, S., and Matzner, Y., Widespread expression of serum amyloid A in histologically normal human tissue. Predominant localization to the epithelium, J. Histochem. Cytochem. 46:1377-1384 (1998).

van der Luijt et al., Genomics 20:1-4 (1994); "Rapid Detection of Translation-Terminating Mutations at the Adenomatous Polyposis Coli (APC) Gene by Direct Protein Truncation Test".

Vaughan, D. et al., In: General Ophthalmology, Appleton & Lange, Norwalk, Conn., pp. 213-230 (1992).

Written Opinion of the International Searching Authority of a related PCT Application No. PCT/USO4/40156, mailed Jul. 26, 2006.

PCT International Search Report of a related PCT Application No. PCT/US2007/087797, with Apr. 16, 2008 mailing date.

* cited by examiner

USE OF SERUM AMYLOID A GENE IN DIAGNOSIS AND TREATMENT OF GLAUCOMA AND IDENTIFICATION OF ANTI-GLAUCOMA AGENTS

The present invention is a continuation-in-part of U.S. application Ser. No. 11/000,757, filed Dec. 1, 2004, which claims priority to U.S. provisional application No. 60/530,430, filed Dec. 17, 2003.

BACKGROUND OF THE INVENTION

1. Field of the Invention

The present invention relates to the field of diagnosis and treatment of glaucoma. More specifically, the invention provides methods and compositions for diagnosing and treating glaucoma and for identifying agents potentially useful for the treatment of glaucoma.

2. Description of the Related Art

There are a number of ocular conditions that are caused by, or aggravated by, damage to the optic nerve head, degeneration of ocular tissues, and/or elevated intraocular pressure. For example, "glaucomas" are a group of debilitating eye diseases that are a leading cause of irreversible blindness in the United States and other developed nations. Primary Open Angle Glaucoma ("POAG") is the most common form of glaucoma. The disease is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head were heavily debated as the major factors causing progression of visual field loss in glaucoma. Since then, other factors including excitotoxicity, nitric oxide, absence of vital neurotrophic factors, abnormal glial/neuronal interplay and genetics have been implicated in the degenerative disease process. The consideration of molecular genetics deserves some discussion insofar as it may ultimately define the mechanism of cell death, and provide for discrimination of the various forms of glaucoma. Within the past 10 years, over 15 different glaucoma genes have been mapped and 7 glaucoma genes identified. This includes six mapped genes (GLC1A-GLC1F) and two identified genes (MYOC and OPTN) for primary open angle glaucoma, two mapped genes (GLC3A-GLC3B) and one identified gene for congenital glaucoma (CYP1B1), two mapped genes for pigmentary dispersion/pigmentary glaucoma, and a number of genes for developmental or syndromic forms of glaucoma (FOXC1, PITX2, LMX1B, PAX6).

Thus, each form of glaucoma may have a unique pathology and accordingly a different therapeutic approach to the management of the disease may be required. For example, a drug that effects the expression of enzymes that degrade the extracellular matrix of the optic nerve head would not likely prevent RGC death caused by excitotoxicity. In glaucoma, RGC death occurs by a process called apoptosis (programmed cell death). It has been speculated that different types of insults that can cause death may do so by converging on a few common pathways. Targeting downstream at a common pathway is a strategy that may broaden the utility of a drug and increase the probability that it may have utility in the management of different forms of the disease. However, drugs that effect multiple metabolic pathways are more likely to produce undesirable side-effects. With the advent of gene-based diagnostic kits to identify specific forms of glaucoma, selective neuroprotective agents can be tested with the aim of reducing the degree of variation about the measured response.

Glaucoma is currently diagnosed based on specific signs of the disease (characteristic optic nerve head changes and visual field loss). However, over half of the population with glaucoma are unaware they have this blinding disease and by the time they are diagnosed, they already have irreversibly lost approximately 30-50% of their retinal ganglion cells. Thus, improved methods for early diagnosis of glaucoma are needed.

Current glaucoma therapy is directed to lowering IOP, a major risk factor for the development and progression of glaucoma. However, none of the current IOP lowering therapies actually intervenes in the glaucomatous disease process responsible for elevated IOP and progressive damage to the anterior segment continues. This is one possible reason why most patients become "resistant" to conventional glaucoma therapies. Thus, what is needed is a therapeutic method for altering (by inhibiting or even reversing) the disease process.

SUMMARY OF THE INVENTION

The present invention overcomes these and other drawbacks of the prior art by providing methods to diagnose and compositions to treat glaucoma. In one aspect, the present invention provides a method for treating glaucoma by administering to a patient in need thereof a therapeutically effective amount of a composition comprising an agent that interacts with a gene encoding serum amyloid A protein (SAA), or with the gene's promoter sequence. The interaction between the agent and the gene encoding SAA, or with its promoter sequence, modulates the expression of SAA, such that the patient's glaucomatous condition is treated. In preferred embodiments, the agent will be a protein, peptide, peptidomimetic, small molecule or nucleic acid.

In another aspect, the present invention provides a method for treating glaucoma by administering to a patient in need thereof a therapeutically effective amount of a composition comprising an agent that inhibits interaction of the serum amyloid A protein (SAA) with its receptor. Preferably, the agent will be a peroxisome proliferator-activated receptor α (PPARα) agonists, tachykinin peptides and their non-peptide analogs or α-lipoic acid. Most preferably, the agent will be fenofibrate, Wy-14643, (4-chloro-6-(2,3-xylidino)-2-pryrimidinylthiol)-acetic acid), ciprofibrate, 2-bromohexadecanoic acid, bezafibrate and ciglitizone, bafilomycin, concanamycin or pseudolaric acid B.

The present invention further provides a pharmaceutical composition for treating glaucoma comprising a therapeutically effective amount of a serum amyloid A protein (SAA) antagonist and a pharmaceutical carrier. The antagonist contained in the composition may be any of the compounds identified above.

In yet another embodiment, the present invention provides a method for diagnosing glaucoma, by the following steps:
a) obtaining a biological sample from a patient; and
b) analyzing said sample for an aberrant level, aberrant bioactivity or mutations of the gene encoding serum amyloid A protein (SAA) or its promoter region or its gene products, wherein said gene encoding SAA comprises the sequence set forth in SEQ ID NO:1 or SEQ ID NO:3, wherein its promoter region comprises the sequence set forth in SEQ ID NO:12 or SEQ ID NO:13, and wherein SAA comprises the sequence set forth in SEQ ID NO:2 or SEQ ID NO:4;
wherein the aberrantly high level, aberrantly high bioactivity or mutations of the SAA genes or the gene products indicates a diagnosis of glaucoma.

In preferred aspects, the biological sample is ocular tissue, tears, aqueous humor, cerebrospinal fluid, nasal or cheek swab or serum. Most preferably, the biological sample comprises trabecular meshwork cells.

Alternatively, the present invention provides a method for diagnosing glaucoma in a patient, by the steps:
a) collecting cells from a patient;
b) isolating nucleic acid from the cells;
c) contacting the sample with one or more primers which specifically hybridize 5' and 3' to at least one allele of SEQ ID NO:1, SEQ ID NO:3, SEQ ID NO:12, or SEQ ID NO:13 under conditions such that hybridization and amplification of the allele occurs; and
d) detecting the amplification product;
wherein aberrant level or mutations of SEQ ID NO:1, SEQ ID NO:3, SEQ ID NO:12, or SEQ ID NO:13, in the sample indicates a diagnosis of glaucoma.

The present invention also provides a method for identifying agents potentially useful for treating glaucoma, by the steps:
a) obtaining cells expressing SAA (SEQ ID NO:1 or SEQ ID NO:2) or cells containing SAA promoter/reporter gene such that the reporter gene is expressed;
b) admixing a candidate substance with the cells; and
c) determining the level of SAA protein (SEQ ID NO:2 or SEQ ID NO:4) or the level of gene expression in the cells;
wherein an increase or decrease of the production of SAA protein or gene expression in the presence of said candidate substance indicates an agent potentially useful for the treatment of glaucoma.

In another aspect, the present invention provides a method for identifying an agent potentially useful for treating glaucoma, by the steps:
a) forming a reaction mixture comprising:
(i) an SAA protein or a cell expressing SAA or a reporter gene driven by an SAA promoter;
(ii) an SAA protein binding partner; and
(iii) a test compound; and
b) detecting interaction of the SAA protein and binding partner or level of reporter gene products in the presence of the test compound and in the absence of the test compound;
wherein a decrease or increase in the interaction of the SAA protein with its binding partner in the presence of the test compound relative to the interaction in the absence of the test compound indicates a potentially useful agent for treating glaucoma.

In another aspect, the present invention provides a method for identifying an agent potentially useful for treating glaucoma, by the steps:
a) forming a reaction mixture comprising:
(i) cells comprising SAA recombinant protein (SEQ ID NO:2 or SEQ ID NO:4) or cells comprising expression vectors comprising SEQ ID NO:1 or SEQ ID NO:3; and
(ii) a test compound; and
b) detecting the effect on downstream signalling (IL-8) in the presence of the test compound and in the absence of the test compound;

wherein a decrease or increase in the downstream signalling in the presence of the test compound relative to the interaction in the absense of the test compound indicates a potentially useful agent for treating glaucoma.

In preferred aspects, the cells containing the SAA protein or expression vectors will be HL-60 cells.

BRIEF DESCRIPTION OF THE DRAWINGS

The following drawings form part of the present specification and are included to further demonstrate certain aspects of the present invention. The invention may be better understood by reference to these drawings in combination with the detailed description of specific embodiments presented herein.

DETAILED DESCRIPTION PREFERRED EMBODIMENTS

Figure 1:
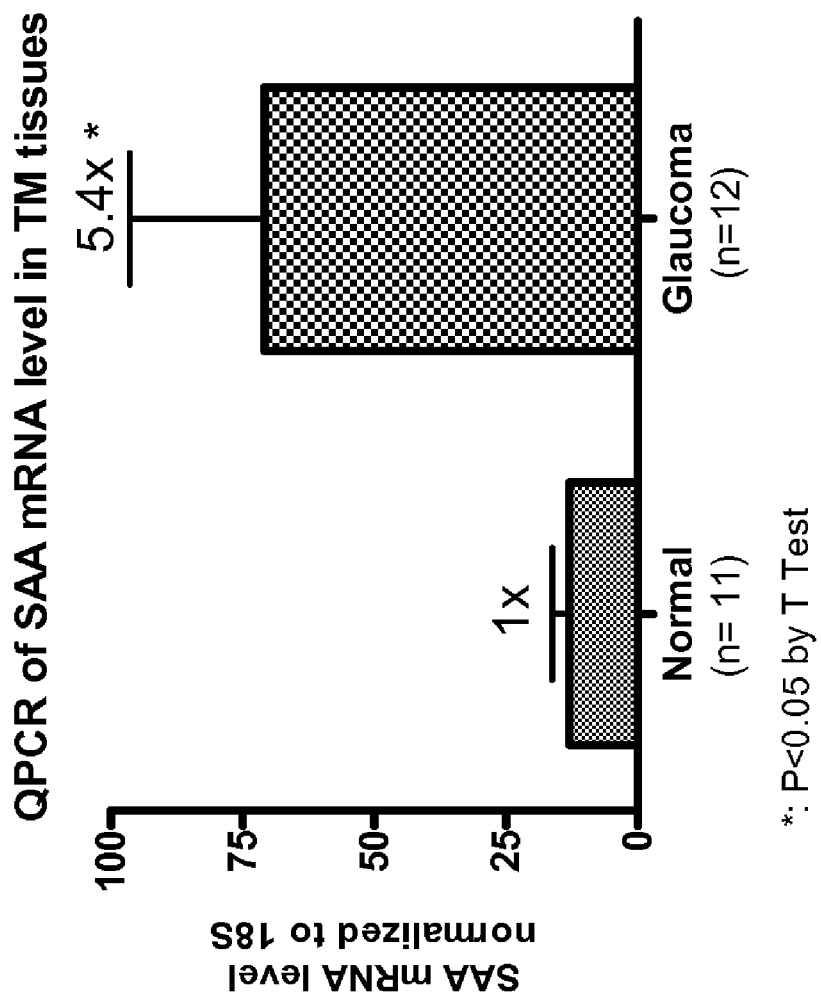
FIG. 1. QPCR analysis of SAA expression in 12 glaucoma vs. 11 normal TM tissues. NTM and GTM represent average expression level of the gene in normal and glaucoma groups, respectively.

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the ONH. One of the main risk factors for the development of glaucoma is the presence of ocular hypertension (elevated intraocular pressure, IOP). IOP also appears to be involved in the pathogenesis of normal tension glaucoma where patients have what is often considered to be normal IOP. The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous optic nerve head (ONH). In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

The present inventors have discovered that the expression of Serum Amyloid A (SAA) mRNA and protein are significantly upregulated in glaucomatous TM tissues and cells. The inventors have verified the differential mRNA expression seen using Affymetrix gene chips by real time quantitative polymerase chain reaction (QPCR) and increased SAA protein levels by SAA ELISA. This is the first time SAA has been shown to be expressed in the TM.

Human SAA comprises a number of small, differentially expressed apolipoproteins encoded by genes localized on the short arm of chromosome 11. There are four isoforms of SAAs. SAA1 (SEQ ID NO:2), encoded by SEQ ID NO:1, and SAA2 (SEQ ID NO:4), encoded by SEQ ID NO:3, are known as acute phase reactants, like C-reactive protein, that is, they are dramatically upregulated by proinflammatory cytokines. The 5'UTR promoter regions of SAA1 and SAA2 genes are also provided (SEQ ID NO:12 and SEQ ID NO:13, respectively). SAA3 (SEQ ID NO:5) is a pseudogene and SAA4 (SEQ ID NO:6) is a low level constitutively expressed gene encoding constitutive SAA4 (SEQ ID NO:7). SAA2 has two isoforms, SAA2α (SEQ ID NO:9), encoded by SEQ ID NO:8, and SAA2β (SEQ ID NO:11), encoded by SEQ ID NO:10, which differ by only one amino acid. SAA1 and SAA2 proteins are 93.5% identical at the amino acid level (SEQ ID NO:2 and SEQ ID NO:4, respectively) and these genes are 96.7% identical at the nucleotide level (SEQ ID NO:1 and SEQ ID NO:3, respectively).

SAA is an acute-phase reactant whose level in the blood is elevated approximately 1000-fold as part of the body's responses to various injuries, including trauma, infection, inflammation, and neoplasia. As an acute-phase reactant, the liver has been considered to be the primary site of expression. However, extrahepatic SAA expression was described initially in mouse tissues, and later in cells of human atherosclerotic lesions (O'Hara et al. 2000). Subsequently, SAA mRNA was found widely expressed in many histologically normal human tissues. Localized expression was noted in a variety of tissues, including breast, stomach, small and large intestine, prostate, lung, pancreas, kidney, tonsil, thyroid, pituitary, placenta, skin epidermis, and brain neurons. Expression was also observed in lymphocytes, plasma cells, and endothelial cells. SAA protein expression co-localized with SAA mRNA expression has also been reported in histologically normal human extrahepatic tissues. (Liang et al. 1997; Urieli-Shoval et al. 1998).

SAA isoforms are apolipoproteins that become a major component of high-density lipoprotein (HDL) in the blood plasma of mammals and displaces A-I (ApoA-I) and phospholipid from the HDL particles (Miida et al. 1999). SAA binds cholesterol and may serve as a transient cholesterol-binding protein. In addition, over-expression of SAA1 or SAA2 leads to the formation of linear fibrils in amyloid deposits, which can lead to pathogenesis (Uhlar and Whitehead 1999; Liang et al. 1997). SAA plays an important role in infections, inflammation, and in the stimulation of tissue repair. SAA concentration may increase up to 1000-fold following inflammation, infection, necrosis, and decline rapidly following recovery. Thus, serum SAA concentration is considered to be a useful marker with which to monitor inflammatory disease activity. Hepatic biosynthesis of SAA is up-regulated by pro-inflammatory cytokines, leading to an acute phase response. Chronically elevated SAA concentrations are a prerequisite for the pathogenesis of secondary amyloidosis, a progressive and sometimes fatal disease characterized by the deposition in major organs of insoluble plaques composed principally of proteolytically cleaved SAA. This same process also may lead to atherosclerosis. There is a requirement for both positive and negative SAA control mechanisms to maintain homeostasis. These mechanisms permit the rapid induction of SAA expression to fulfill host-protective functions, but they also must ensure that SAA expression is rapidly returned to baseline levels to prevent amyloidosis. These mechanisms include modulation of promoter activity involving, for example, the inducer nuclear factor kB (NF-kB) and its inhibitor IkB, up-regulation of transcription factors of the nuclear factor for interleukin-6 (NF-IL6) family, and transcriptional repressors such as yin and yang 1 (YY1). Post-transcriptional modulation involving changes in mRNA stability and translation efficiency permit further up- and down-regulatory control of SAA protein synthesis to be achieved. In the later stages of the AP response, SAA expression is effectively down-regulated via the increased production of cytokine antagonists such as the interleukin-1 receptor antagonist (IL-1Ra) and of soluble cytokine receptors, resulting in less signal transduction driven by pro-inflammatory cytokines (Jensen and Whitehead 1998).

There are several reports suggesting that primary amyloidosis may be associated with glaucoma. For example, it was found that amyloid was deposited in various ocular tissues including the vitreous, retina, choroid, iris, lens, and TM in primary systemic amyloidosis patients (Schwartz et al. 1982). Ermilov et al. (1993) reported that in 478 eyes of 313 patients, aged 25 years to 90 years, with cataracts, glaucoma, and/or diabetes mellitus, 66 (14%) of the eyes contained amyloid-pseudoexfoliative amyloid (PEA). Krasnov et al. (1996) reported that 44.4% of 115 patients with open-angle glaucoma revealed extracellular depositions of amyloid. Amyloidosis was revealed in the sclera in 82% of the cases and in the iris in 70% of the cases. A number of clinical conditions, including Alzheimer's disease, exhibit aberrant amyloid tissue deposits associated with disease. However, amyloids are molecularly heterogeneous and encoded by different amyloid genes. The previous reports are unclear regarding which amyloid(s) might be associated with glaucoma. The present inventors have shown, for the first time, that SAA gene expression is elevated significantly in glaucomatous TM tissues. Increased SAA may be involved in the generation of elevated IOP and damage to the optic nerve leading to vision loss in glaucoma patients. The present invention provides methods of using a finding of increased SAA expression to diagnose glaucoma. The present invention further provides methods for screening for agents that alter SAA expression or function in order to identify potentially anti-glaucomatous agents. In another aspect, the present invention provides methods and compositions of using agents that antagonize SAA actions and/or interactions with other proteins for the treatment of glaucoma.

Diagnosing Glaucoma

Based on the inventors' finding that certain subjects with glaucoma have increased levels of SAA expression, the present invention provides a variety of methods for diagnosing glaucoma. Certain methods of the invention can detect mutations in nucleic acid sequences that result in inappropriately high levels of SAA protein. These diagnostics can be developed based on the known nucleic acid sequence of human SAA, or the encoded amino acid sequence (see Miller 2001). Other methods can be developed based on the genomic sequence of human SAA or of the sequence of genes that regulate expression of SAA. Still other methods can be developed based upon a change in the level of SAA gene expression at the mRNA level.

In alternative embodiments, the methods of the invention can detect the activity or level of SAA signaling proteins or genes encoding SAA signaling proteins. For example, methods can be developed that detect inappropriately low SAA signaling activity, including for example, mutations that result in inappropriate functioning of SAA signaling components, including SAA induction of IL-8. In addition, non-nucleic acid based techniques may be used to detect alteration in the amount or specific activity of any of these SAA signaling proteins.

A variety of means are currently available to the skilled artisan for detecting aberrant levels or activities of genes and gene products. These methods are well known by and have become routine for the skilled artisan. For example, many methods are available for detecting specific alleles at human polymorphic loci. The preferred method for detecting a specific polymorphic allele will depend, in part, upon the molecular nature of the polymorphism. The various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. A variety of methods are available for detecting the presence of a particular single nucleotide polymorphic allele in an individual. Advancements in the field have provided accurate, easy, and inexpensive large-scale SNP genotyping. For example, see U.S. Pat. No. 4,656,127; French Patent 2,650,840; PCT App. No. WO91/02087; PCT App. No. WO92/15712; Komher et al. 1989; Sokolov 1990; Syvanen et al. 1990; Kuppuswamy et al. 1991; Prezant et al. 1992; Ugozzoli et al. 1992; Nyren et al. 1993; Roest et al. 1993; and van der Luijt et al. 1994).

Any cell type or tissue may be utilized to obtain nucleic acid samples for use in the diagnostics described herein. In a preferred embodiment, the DNA sample is obtained from a bodily fluid, e.g., blood, obtained by known techniques (e.g. venipuncture), or buccal cells. Most preferably, the samples for use in the methods of the present invention will be obtained from blood or buccal cells. Alternately, nucleic acid tests can be performed on dry samples (e.g. hair or skin).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo 1992).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an SAA signaling component that is indicative of glaucoma and having about 5, 10, 20, 25 or 30 contiguous nucleotides around the mutation or polymorphic region. In a preferred embodiment of the invention, several probes capable of hybridizing specifically to other allelic variants involved in glaucoma are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996). In one embodiment, a chip comprises all the allelic variants of at least one polymorphic region of a gene. The solid phase support is then contacted with a test nucleic acid and hybridication to the specific probes is detected. Accordingly, the identity of numerous allelic variants of one or more genes can be identified in a simple hybridization experiment.

These techniques may further include the step of amplifying the nucleic acid before analysis. Amplification techniques are known to those of skill in the art and include, but are not limited to, cloning, polymerase chain reaction (PCR), polymerase chain reaction of specific alleles (ASA), ligase chain reaction (LCR), nested polymerase chain reaction, self sustained sequence replication (Guatelli et al. 1990), transcriptional amplification system (Kwoh et al. 1989), and Q-Beta Replicase (Lizardi, et al. 1988).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, SSCP, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of SAA that is indicative of glaucoma under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, aberrant levels or activities of SAA that are indicative of glaucoma are identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed my Maxim and Gilbert (1977) or Sanger (1977). It is also contemplated that any of a variety of automated sequencing procedures may be utilized when performing the subject assays, including sequencing by mass spectrometry (see, for example WO94/16101; Cohen et al. 1996; Griffin et al. 1993). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamin or osmium tetraoxide and with piperidine) can be used to detect mismatched bases in RNA/RNA or RNA/DNA or DNA/DNA heteroduplexes (Myers et al. 1985b; Cotton et al. 1988; Saleeba et al. 1992). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T and G/T mismatches (Hsu et al. 1994; U.S. Pat. No. 5,459,039).

In other embodiments, alterations in electrophoretic mobility will be used to identify aberrant levels or activities of SAA that are indicative of glaucoma. For example, single strand conformation polymorphism (SSCP) may be used to detect differences in electrophoretic mobility between mutant and wild type nucleic acids (Orita et al. 1989; Cotton 1993; Hayashi 1992; Keen et al. 1991).

In yet another embodiment, the movement of alleles in polyacrylamide gels containing a gradient of denaturant is assayed using denaturing gradient gel electrophoresis (DGGE) (Myers et al. 1985a). In a further embodiment, a temperature gradient is used in place of a denaturing agent gradient to identify differences in the mobility of control and sample DNA (Rosenbaum and Reissner 1987).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. 1986; Saiki et al. 1989). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al. 1989) or at the extreme 3' end of one primer where, under appropriate conditions, mismatch can prevent, or reduce polymerase extension (Prossner 1993). In addition it may be desirable to introduce a novel restriction site in the region of the mutation to create cleavage-based detection (Gasparini et al. 1992). It is anticipated that in certain embodiments amplification may also be performed using Taq ligase for amplification (Barany 1991). In such cases, ligation will occur only if there is a perfect match at the 3' end of the 5' sequence making it possible to detect the presence of a known mutation at a specific site by looking for the presence or absence of amplification.

In another embodiment, identification of an allelic variant is carried out using an oligonucleotide ligation assay (OLA), as described, E.g., in U.S. Pat. No. 4,998,617 and in Landegren et al. 1988). Nickerson et al. have described a nucleic acid detection assay that combines attributes of PCR and OLA (Nickerson et al. 1990). In this method, PCR is used to achieve the exponential amplification of target DNA, which is then detected using OLA.

Several techniques based on this OLA method have been developed and can be used to detect aberrant levels or activities of SAA that are indicative of glaucoma. For example, U.S. Pat. No. 5,593,826 and Tobe et al. (1996), describe such techniques that are frequently used.

In one embodiment, fenofibrate, a peroxisome proliferator-activated receptor α (PPARα) agonist, may be formulated in a pharmaceutically acceptable composition and used to treat glaucoma by modulating SAA expression. Studies have shown that fenofibrate and WY 14643 treatment reduces plasma SAA concentration (Yamazaki et al. 2002). It is believed that other PPARα agonists, such as ciprofibrate, 2-bromohexadecanoic acid, bezafibrate, ciprofibrate and ciglitizone may also be useful for the treatment of glaucoma.

Figure 11:
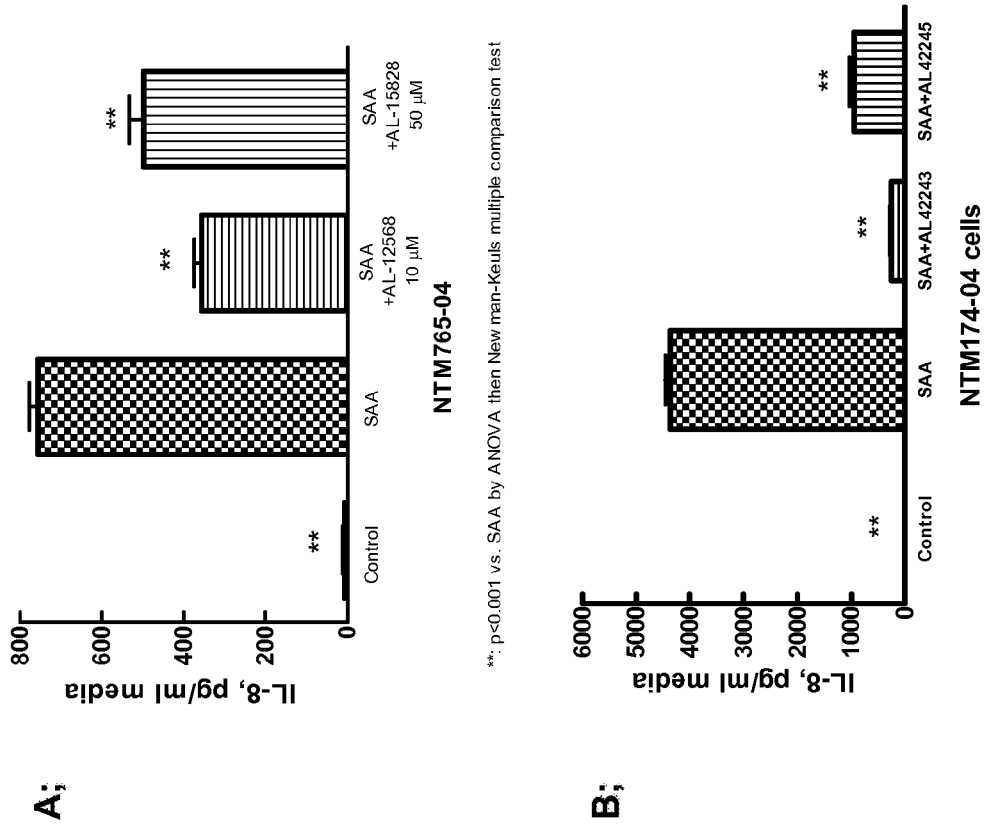
FIG. 11. Effect of MAP p38 kinase inhibitors on induction of IL-8 by SAA treatment (1 μg/ml) in TM cells. A: Effect of SB203580 (4-(4-fluorophenyl)-2-(4-methylsulfinylphenyl)-5-(4-pyridyl)-1H-imidazole). B: Effect of 4-azaindole and BIRB-796 (1-(5-tert-butyl-2-p-tolyl-2H-pyrazol-3-yl)-3(4-(2-morpholin-4-yl-ethoxy)naph-thalen-1-yl)urea) at 50 μM. IL-8 was measured in the media by ELISA.
Figure 12:
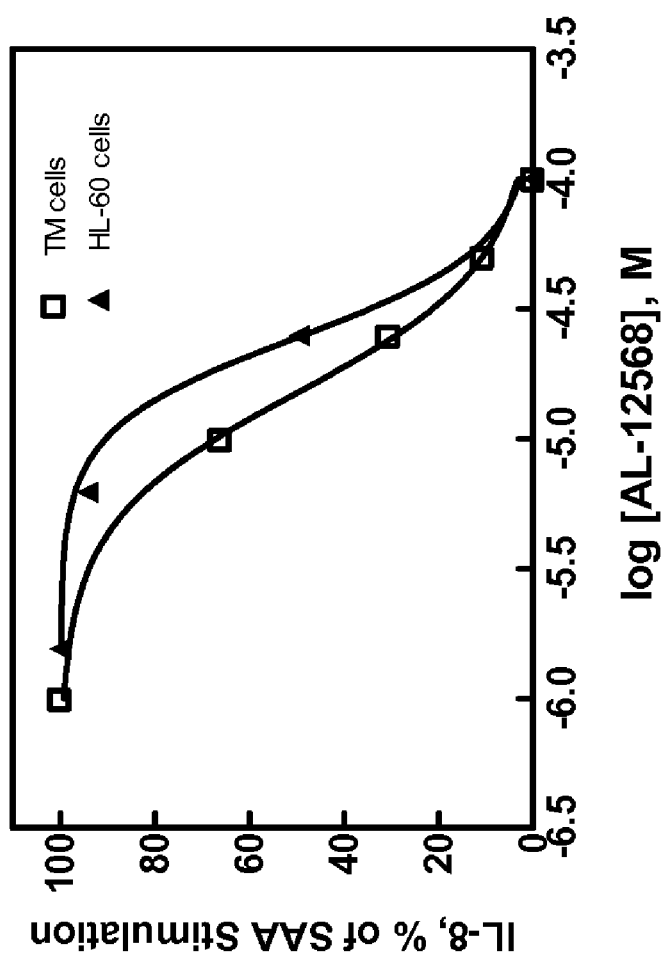
FIG. 12. Inhibition of SAA stimulated IL-8 secretion by SB203580 in TM cells and HL-60 cells. NTM650-03, p9 or HL-60 cells were treated in serum-free DMEM for 4 hours with 1 μg/ml SAA and the indicated concentrations of SB202580. IL-8 was measured in the media by ELISA. Calculated $IC_{50}$=15 μM in TM cells and 25 μM in HL-60 cells.
Figure 13:
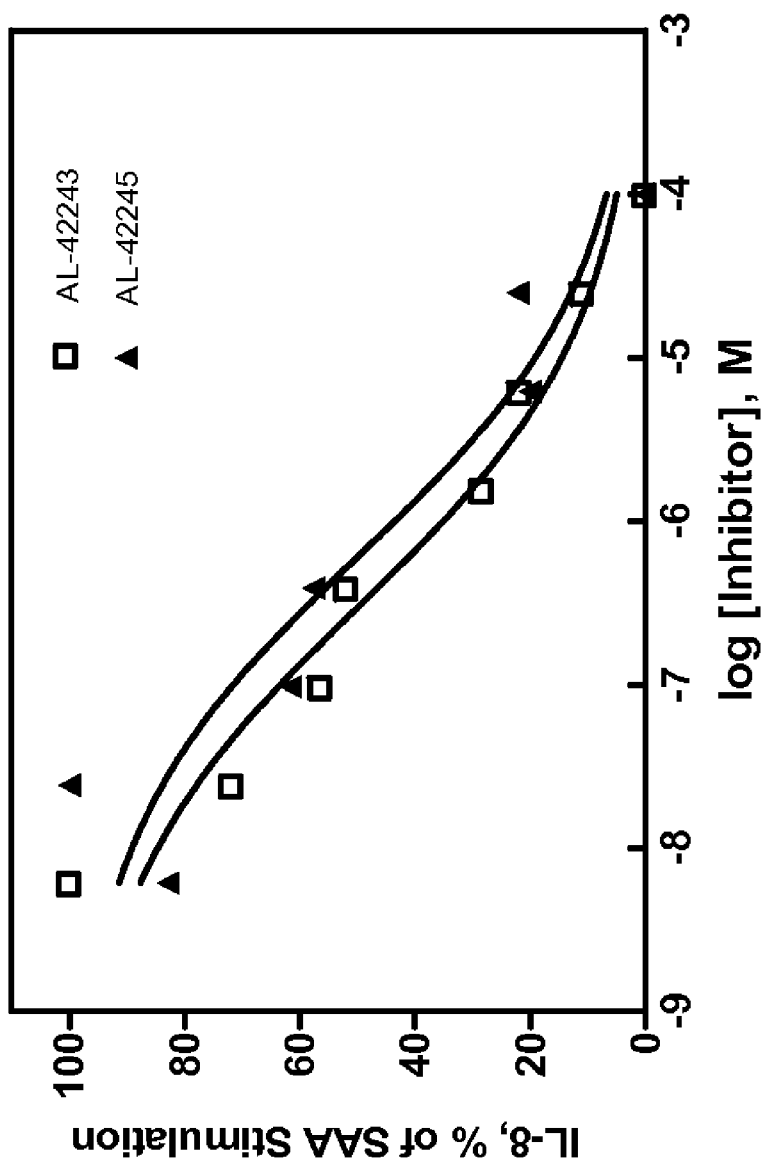
FIG. 13. Inhibition of SAA stimulated IL-8 secretion by the p38 MAP kinase inhibitors, 4-azaindole and BIRB-796 in HL60 cells treated in serum-free DMEM for 4 hours with 1 μg/ml SAA and the indicated concentrations of inhibitors. IL-8 was measured in the media by ELISA. Calculated $IC_{50}$: 4-azaindole=0.3 μM, BIRB-796=0.5 μM.

In another embodiment, p38 MAP kinase inhibitors may be used to treat glaucoma by modulating SAA induced expression of IL-8 and downstream signaling events. The inventors showed that SAA stimulates secretion of IL-8 in trabecular meshwork cells and tissue. One pathway for upregulation of IL-8 is through activation of MAP kinases. The inventors further showed that inhibitors of p38 MAP kinase block SAA induction of IL-8 in TM cells, in perfusion cultured human eyes, and in vivo in rodent eyes. Compounds representing different classes of MAPK inhibitors in TM cells were found to be effective inhibitors of SAA induced IL-8 expression (Table 3). The most potent of these were the p38 MAPK inhibitors, SB203580, 4-azaindole, and BIRB-796 (FIG. 11). Dose response curves for SB203580 inhibition of SAA induced IL-8 generated in both TM cells and HL60 cells gave similar results ($IC_{50}$=15 µM in TM cells and 25 µM in HL60 cells, FIG. 12). Inhibition curves for 3-(4-fluorophenyl)-2-(pyridin-4-yl)-1H-pyrrolo[3,2-b]pyridine (also referred to herein as a 4-azaindole) and BIRB0796 conducted in HL60 cells showed both of these compounds to be approximately 10 times more effective than SB203580 ($IC_{50}$=0.3 for 4-azaindole and 0.5 µM for BIRB-796 (FIG. 13).

to additional classes of compounds that exibit inhibitory properties for p38MAP kinases as described in these examples and include SB202190, SB203580, SB220025, PD 169316, SB 239063, 4-azaindole, BIRB-796, CalBio506126.

The present inventors further postulate that agents that prevent amyloid-induced cell death may be useful for protecting TM and other ocular cells in the anterior uvea and at the back of the eye, especially the retina and optic nerve head.

The Compounds of this invention, can be incorporated into various types of ophthalmic formulations for delivery to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Oph-

TABLE 3

Compound Classes Screened for Inhibition of SAA Induced IL-8 Secretion in TM Cells

| Compound | Target | Selectivity | % Inhibition of SAA induced IL-8 secretion | | | | |
|---|---|---|---|---|---|---|---|
| | | | 100 µM | 50 µM | 25 µM | 10 µM | 1 µM |
| SB203580 | MAPK | p38 MAP kinase | 98.7 | 73.8 | 61.0 | 38.1 | 16.3 |
| SB202190 | MAPK | p38 MAP kinase | | 38.2 | | 43.3 | 17.2 |
| BIRB-796 | MAPK | p38 MAP kinase | | 78.1 | | 28.9 | |
| 4-azaindole | MAPK | p38 MAP kinase | | 94.3 | | 22.6 | |
| PD98059 | MAPK | MEK | | 34.0 | | | |
| U0126 | MAPK | MEK | | 53.0 | | 50.6 | 30.9 |
| Fenofibrate | SAA | PPARα agonist | | 57.2 | | 52.7 | 59.9 |

Figure 8:
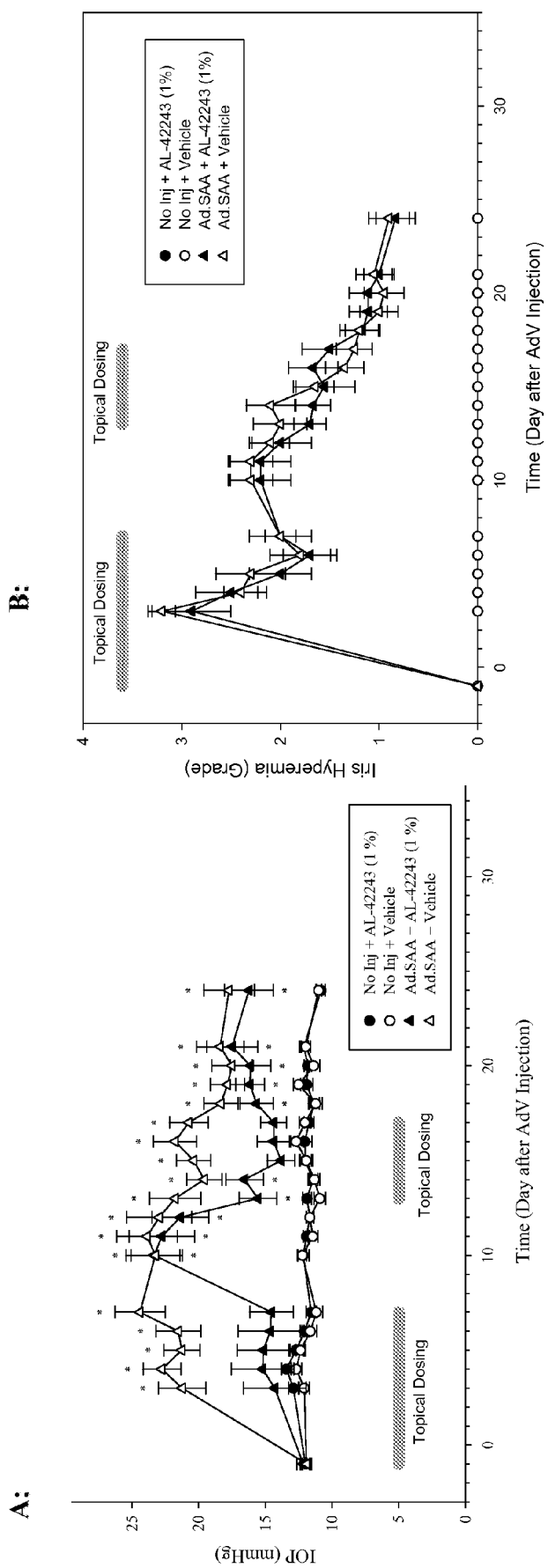
FIG. 8A and FIG. 8B. Effect of intravitreal injection of Ad.SAA2+anti-CD40L antibody on Balb/c mouse IOP (FIG. 8A) and iris hyperemia (FIG. 8B). Data are presented as mean and SEM.

Chemical names for the compounds identified in Table 3 are as follows:
SB203580: 4-(4-fluorophenyl)-2-(4Omethylsulfinylphenyl)-5-(4-pyridyl)-1H-imidazole;
SB202190: 4-[4-(4-fluorophenyl)-5-(4-pyridinyl)-1H-imidazol-2-yl]phenol;
BIRB-796: 1-(5-tert-butyl-2-p-tolyl-2H-pyrazol-3-yl)-3(4-(2-morpholin-4-yl-ethoxy)naphthalen-1-yl)urea;
4-azaindole: 3-(4-fluorophenyl)-2-(pyridin-4-yl)-1H-pyrrolo[3,2-b] pyridine;
PD98059: 2'-amino-3'-methoxyflavone;
U0126: 1,4-diamino-2,3-dicyano-1,4-bis(2-aminophynyltio)butadiene;
CalBio506126: 2-(4-chlorophenyl)-4-(4-fluorophenyl)-5-pyridin-4-yl-1,2-dihydropyrazol-3-one In vitro assays showed that several p38MAPK inhibitors significantly blocked IL-8 induction by SAA. 3-(4-fluorophenyl)-2-(pyridine-4-yl)-1H-pyrrolo-[3,2-b]pyridine, one of most potent p38 MAPK inhibitors was evaluated for lowering IOP in the mouse by topical application of a 1% suspension after intravitreal injection of Ad.SAA2 ($2\times10^7$ pfu/eye)+antiCD40L. Adv.SAA2, caused a significant IOP elevation, which peaked at days 10-12 with 10-12 mmHg increase from baseline, followed by a slow decline. At day 24, the IOP was 6-7 mmHg above baseline. The ocular hypertension was blocked by topical administration of 4-azaindole (1%; b.i.d.). After 4-azaindole administration was stopped at Day 7, IOP returned to the same level as the vehicle-treated Ad.SAA2-injected group. When drug administration was resumed at day 13, IOP was again lowered to baseline in 3 days (FIG. 8). This experiment was repeated and similar results were obtained. The in vivo data showed that the p38MAPK inhibitor, 4-azaindole, can counteract ocular hypertension induced by Ad.SAA2.

Preferred compounds for this embodiment of the invention are those classes of compounds listed in Table 3, and extends thalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the Compound in a hydrophilic base prepared from the combination of, for example, carbopol-974, or the like, according to the published formulations for analogous ophthalmic preparations; preservatives and tonicity agents can be incorporated.

The Compounds are preferably formulated as topical ophthalmic suspensions or solutions, with a pH of about 4 to 8.

The establishment of a specific dosage regimen for each individual is left to the discretion of the clinicians. The Compounds will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

The Compounds can also be used in combination with other agents for treating glaucoma, such as, but not limited to, β-blockers, prostaglandins, carbonic anhydrase inhibitors, $\alpha_2$ agonists, miotics, and neuroprotectants.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Increased Expression of SAA1 and SAA2 in Glaucomatous TM Cells and Tissues

Figure 2A:
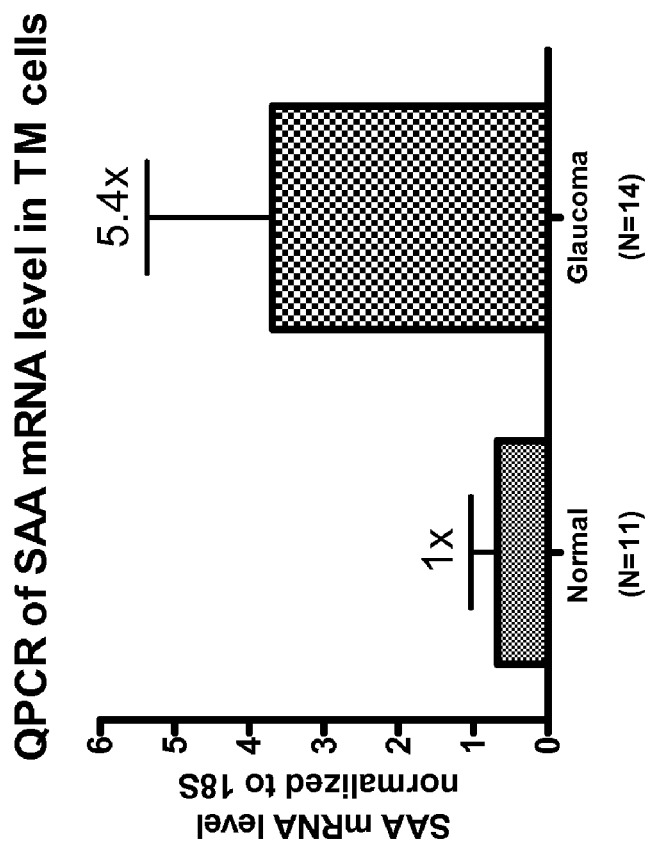
FIG. 2A. QPCR analysis of SAA expression in TM cell lines. NTM and GTM represent average expression level of the gene in normal and glaucoma groups, respectively.
Figure 2B:
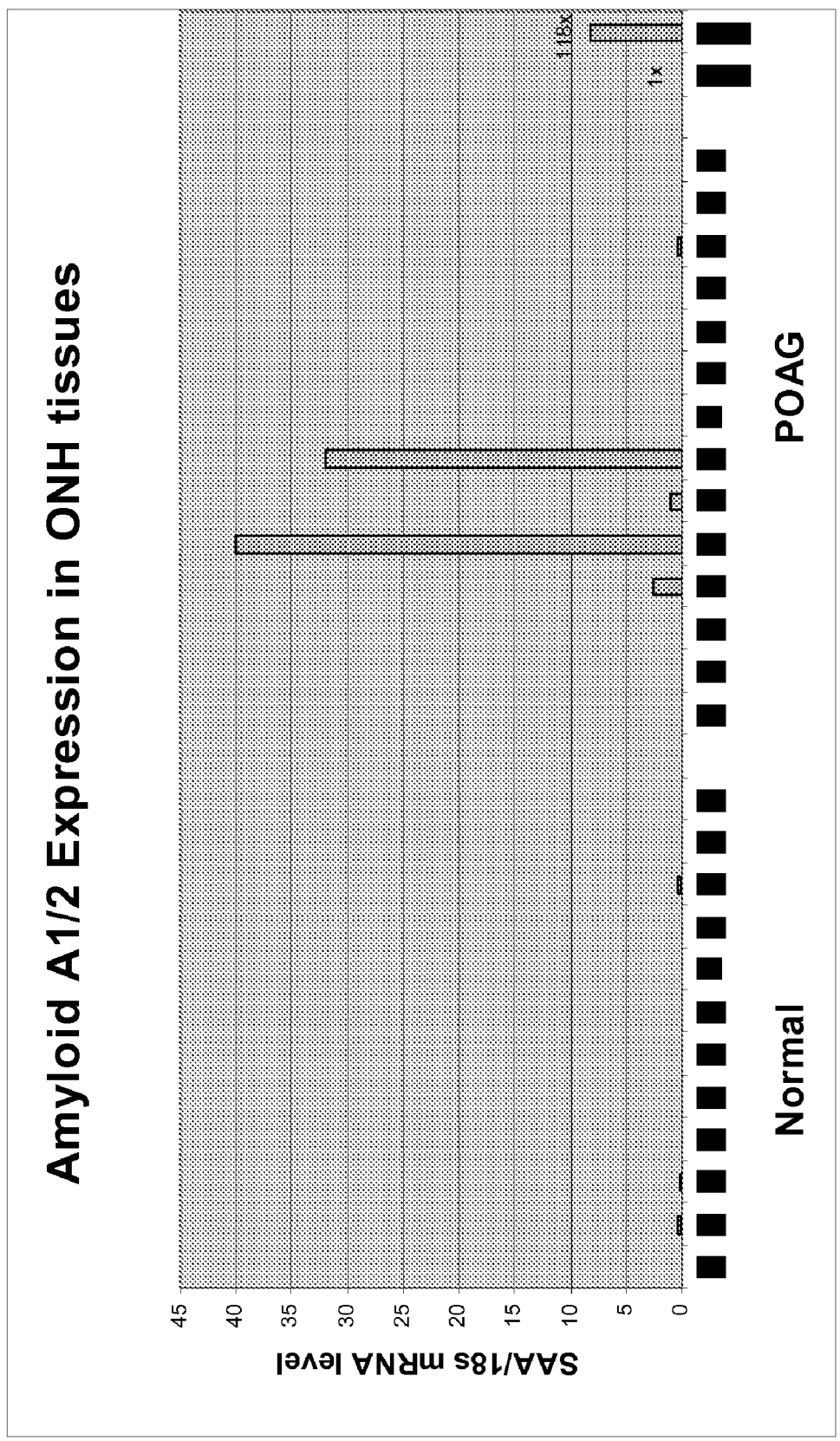
FIG. 2B. QPCR analysis of SAA expression in optic nerve head tissues. NTM and GTM represent average expression level of the gene in normal and glaucoma groups, respectively.
Figure 3:
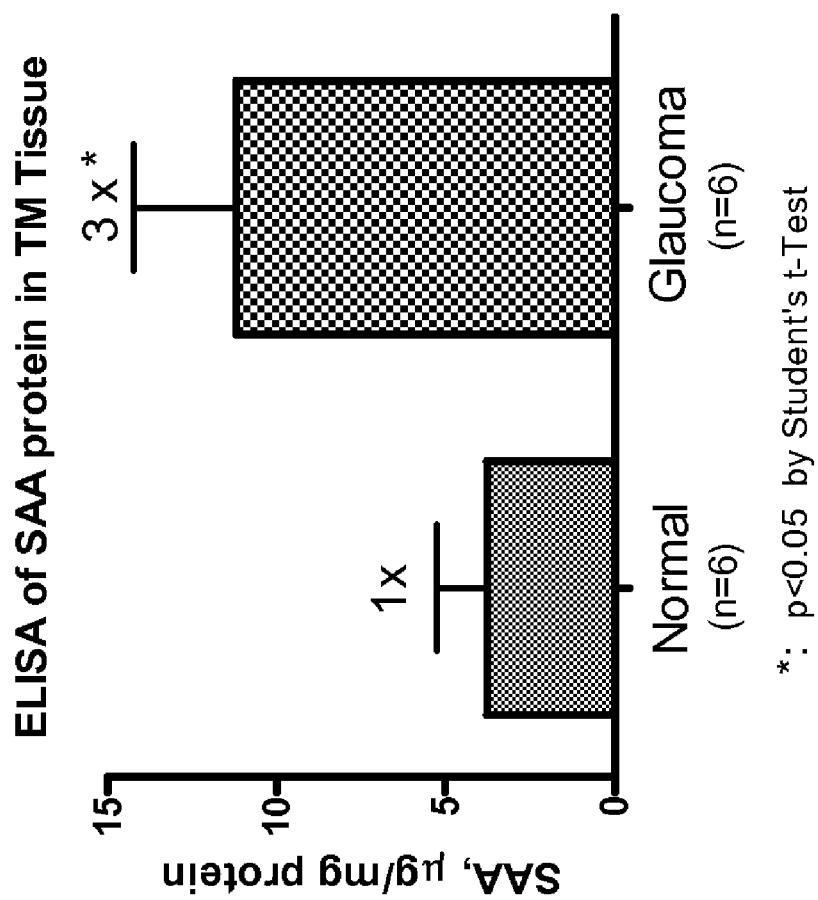
FIG. 3. SAA protein in TM tissues from normal and glaucoma donors (n=6). A significant increase (3-fold) in SAA was observed in glaucoma TM tissues compared to normal tissue (p=0.05). The bars show mean+/−s.e.m.

RNA pools of TM tissues from 13 normal donors vs. 9 glaucoma donors was used to determine gene expression using the Affymetric GeneChips set (HG-U133). Amyloid A2 expression was identified to increase 4 fold in glaucoma comparing to that in normal TM tissues. To confirm this result, QPCR was conducted using individual RNA from 12 glaucoma and 11 normal TM tissues. Five from 12 glaucoma TM tissues (42%) showed significant increase in SAA1/2 expression. Average of SAA expression in the 12 glaucoma TM was 5.4 fold to that in the 11 normal TM (FIG. 1). In addition, a similar trend of SAA differential expression was observed in glaucoma TM cells or glaucoma optic nerve head tissues. There was an average increase of 5.4-fold in glaucoma TM cells (14 glaucoma vs. 11 normal TM cell lines, FIG. 2A) and 118-fold in glaucoma optic nerve head tissues (14 glaucoma vs. 12 normal, FIG. 2B) compared to normals, respectively. ELISA of SAA in TM tissues from 6 normal and 6 glaucoma donors showed that SAA protein was also significantly increased in glaucoma TM tissues compared to normals. There was a 3-fold difference in SAA concentration in glaucomatous tissue compared to normal tissue (11.3 and 3.8 µg/mg protein respectively). These data are shown in FIG. 3.

Figure 4:
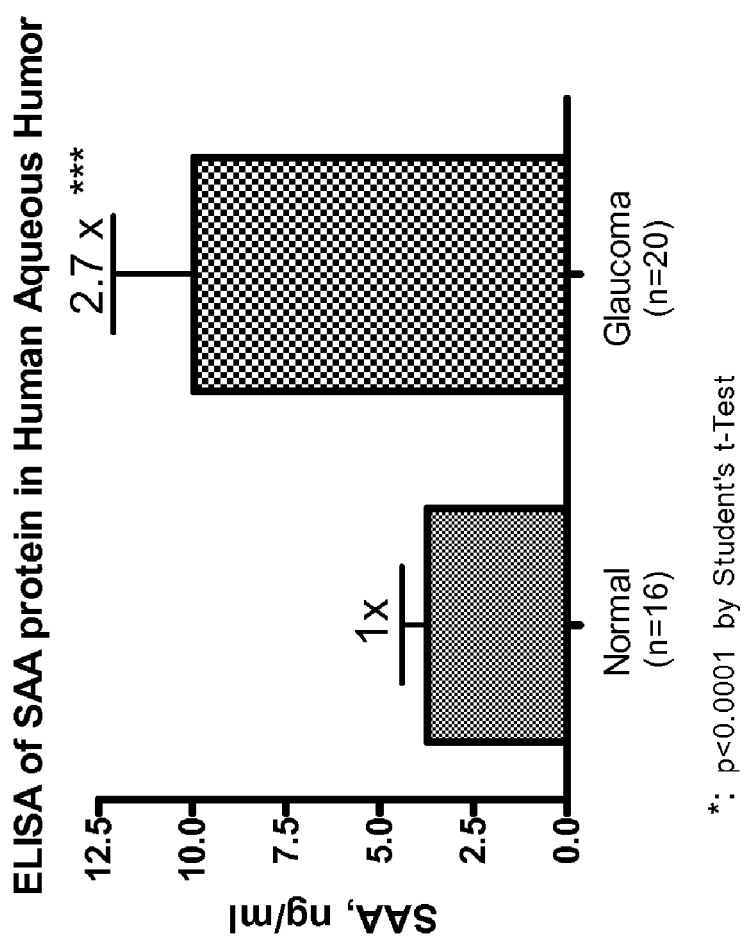
FIG. 4. SAA protein determined by ELISA in human aqueous humor from normal and glaucomatous individuals. The values are expressed as the average SAA in ng/ml of aqueous humor, +/−s.e.m. (p=0.0001).

An association of increased expression of SAA with glaucoma was further demonstrated in human aqueous humor. SAA protein was measured by ELISA in aqueous humor from 16 normal and 20 glaucomatous individuals. SAA was found to be almost 3 times higher in glaucomatous aqueous humor than in normal samples (10.0 ng/ml vs. 3.7 ng/ml respectively). The results are shown in FIG. 4.

EXAMPLE 2

Formulation of Fenofibrate for Topical Application

| 1% Fenofibrate suspension for topical application to decrease SAA and lower IOP in the eye. | | | |
|---|---|---|---|
| Description | Conc. | Units | Purpose |
| Fenofibrate, NOC | 1% | W/V % | active ingredient |
| hydroxypropyl methylcellulose | 0.5% | W/V % | viscosity modifier (2910) (E4M), USP |
| dibasic sodium phosphate | 0.2% | W/V % | buffering agent (anhydrous), usp |
| sodium chloride, usp | 0.75% | W/V % | tonicity agent |
| disodium edta | 0.01% | W/V % | chelating agent (edetate disodium), usp |
| polysorbate 80, nf | 0.05% | W/V % | wetting agent |
| benzalkonium chloride, nf | 0.01% | W/V % | preservative |
| sodium hydroxide, nf | q.s. pH | W/V % | pH adjust |
| hydrochloric acid, nf | q.s. pH | W/V % | pH adjust |
| purified water, usp | q.s. 100% | W/V % | vehicle |

EXAMPLE 3

Procedure for Screening and Identifying Compounds that Alter the Expression of SAA mRNA or SAA Proteins One method that can be used for screening for agents that alter SAA expression and function is to determine changes in SAA protein levels. Kits for in vitro assay for quantitative determination of Serum Amyloid A (SAA) in animal or human sera, plasma, buffered solutions, cell culture media, and tissue or cell extracts are commercially available. The assay is a solid phase sandwich Enzyme Linked-Immuno-Sorbent Assay (ELISA). A monoclonal antibody specific for SAA has been coated onto the wells of a microtiter plate. Samples, including standards of known SAA content, or unknowns, are added to these wells along with a secondary antibody conjugated to alkaline phosphatase or peroxidase. The antibodies are constructed such that neither one interferes with the binding epitope of the other. The SAA is both captured on the plate by the immobilized antibody and labeled with the conjugated second antibody in a one step procedure. After an incubation period, the plate is washed to remove all unbound material and a substrate is (PNPP or peroxide) is added. The intensity of the colored product is proportional to the concentration of SAA present in the unknown sample.

EXAMPLE 4

Induction of SAA in Cultured Cell Lines for Screening Compounds that Alter the Expression of SAA mRNA or Protein The human hepatoma cell line, HepG2, is widely used for studies on SAA induction by cytokines, for transfection with plasmids, and reporter assays. SAA mRNA and protein synthesis can be induced by various cytokines in several human hepatoma cell lines including PCL/PRF/5, HepB and HepG2 (Uhlar and Whitehead 1999). SAA synthesis by human aortic smooth muscle cells (HASMC) is induced by glucocorticoid hormones and not by the proinflammatory cytokines, IL-1, IL-6, and TNF-α, which stimulate the production of SAA by hepatocytes (Kumon et al. 2002b; Kumon et al. 2001; Thorn and Whitehead 2002). SAA stimulated the chemotactic migration of HASMC in a dose dependent manner when assayed using a Chemotaxicell culture chamber (Kumon et al. 2002a). SAA mRNA expression and protein production was demonstrated in primary cultures of rheumatoid arthritis synoviocytes (O'Hara et al. 2000).

EXAMPLE 5

Functional Analysis of SAA in Cultured Cells

Figure 5:
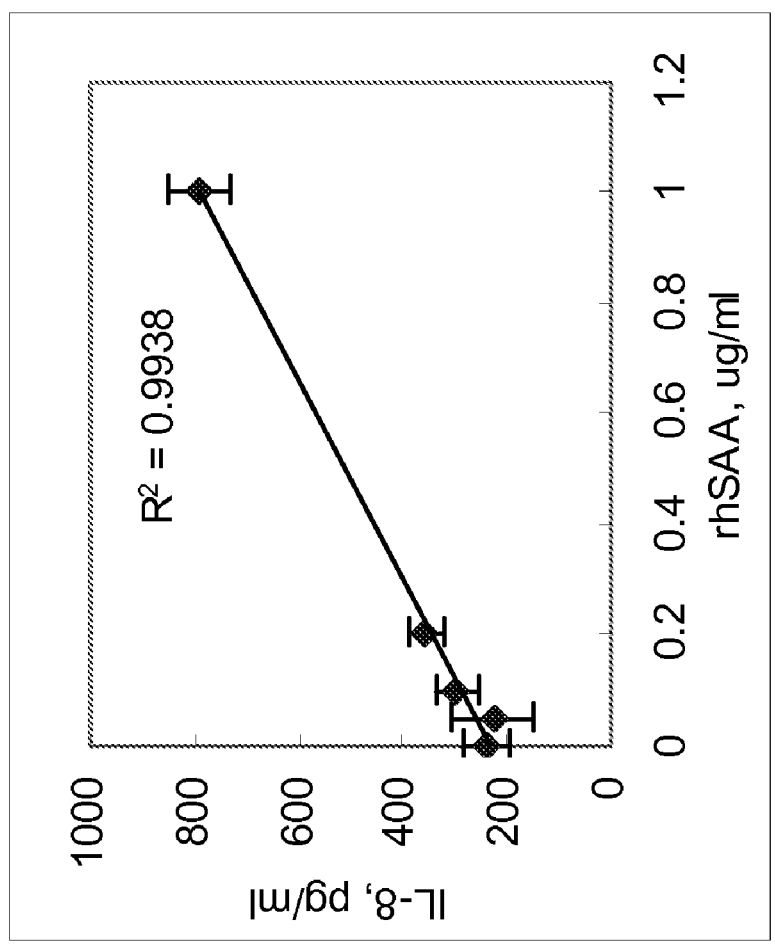
FIG. 5. IL-8 secretion by HL-60 cells in response to increasing concentrations of rhSAA.

Cytokine-like properties of SAA include induction of IL-8 secretion by neutrophils. (Furlaneto and Campa, 2002; He et al. 2003). HL-60 cells, a promyelocytic cell line, was identified that responds to SAA with increased IL-8 secretion, and can be used for in vitro assays of SAA function. HL-60 cells were treated for four hours with increasing concentrations of recombinant human SAA, and IL-8 was measured in the media by ELISA. IL-8 secretion increased in a dose dependent manner (FIG. 5). HL-60 cells can be used as a surrogate cell line for functional assays to identify agents that alter SAA function and expression levels.

EXAMPLE 6

Adenovirus Mediated SAA Expression Increases IOP and p38 MAPK Inhibitor Decreases the Induced IOP in the Mouse The ability of upregulated SAA expression through adenovirus to elevate IOP and efficacy of p38 MAPK inhibitors in blockage of the induced IOP in mouse was studied.

1. Upregulated SAA Expression Elevates IOP in Mouse

Figure 6:
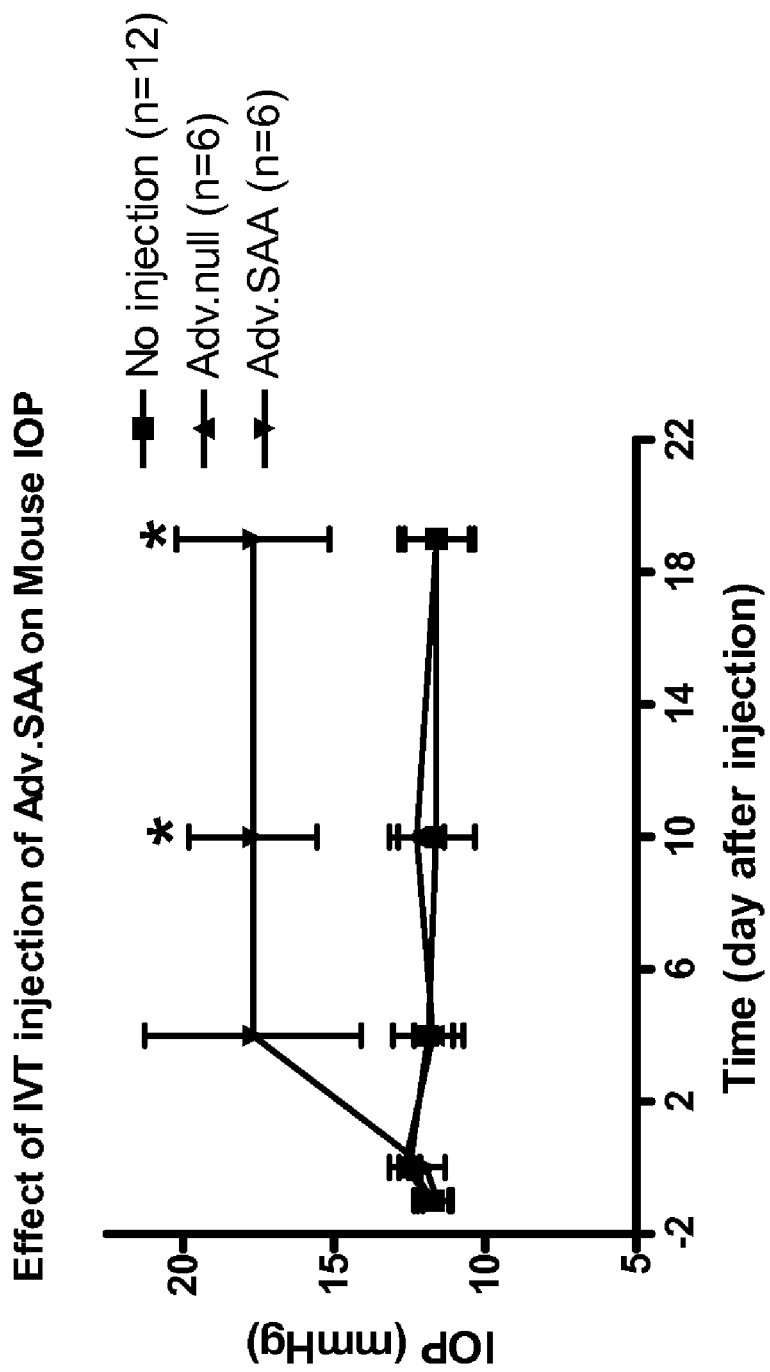
FIG. 6. Effect of Adv.SAA2 on mouse IOP by intravitreal injection. IOP was measured with the rebound tonometers TonoLab®.
Figure 7:
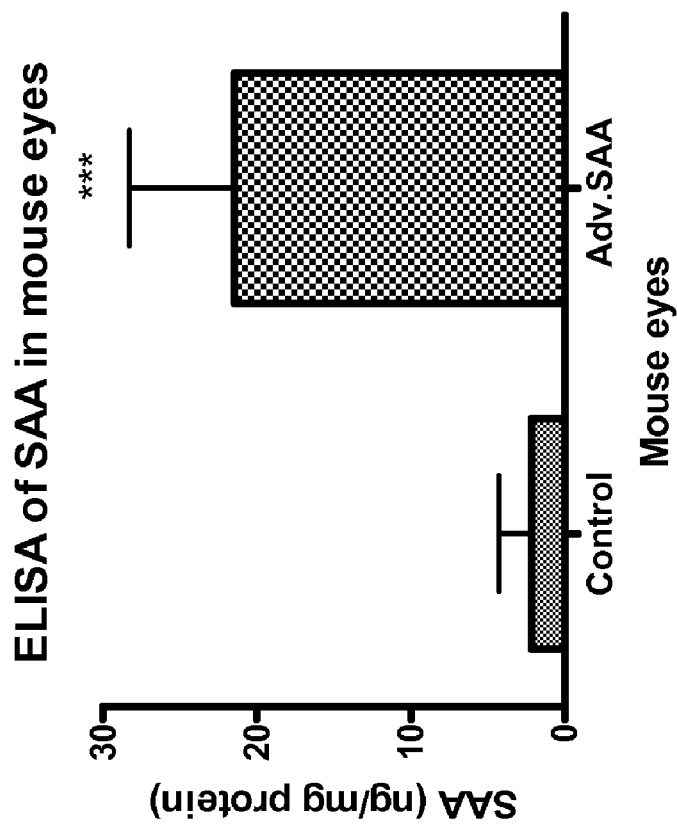
FIG. 7. SAA expression in mouse eyes from Balb/c mice 28 days after intravitreal injection. SAA was measured by ELISA. Control: Adv.null injected eyes and no injection eyes (contralateral eyes of Adv.SAA2 injected eyes; n=16); Adv.SAA: Adv.SAA2 injected eyes (n=17).

One eye of each Balb/c mice was intravitreally injected with Adv.SAA2 (treatment) or Adv.null (vehicle) at dosage of $7 \times 10^7$ pfu/eye/2 ul. Contralateral eye of each animal was not injected. In addition to Adv, each animal received IP injection of anti-CD40L (0.5 mg/injection) on days −1, 0, 1, 2, 5, 9, & 14 to prolong the expression period of the Adv.SAA2. Mouse IOP was measured by Tonolab in a mask way. Mean of IOP for each eye was obtained from 18 to 30 measurements. Intravitreal injection of Adv.SAA2 in mice significantly increased IOP (49% or 5.8 mm Hg, n=6-8, p<0.05) (FIG. 6). SAA expression was significantly higher in all Adv.SAA2 treated eyes than that in control eyes including vehicle treated eyes and contralateral eyes without injection (p<0.0001; n=16) (FIG. 7). These results demonstrated that upregulating SAA expression can increase mouse IOP, providing evidence of SAA linkage to glaucoma pathogenesis.

2. p38 MAPK Inhibitor Lowers Adv.SAA2 Induced IOP in Mouse:

After establishing that 4-azaindole, a P38 MAPK inhibitor inhibits the SAA-induced IL-8 expression in vitro, the inventors tested the effect of the compound on mouse IOP after intravitreal injection of Ad.SAA2 ($2 \times 10^7$ pfu)+antiCD40L by topical administration of 5 μL of 1% 4-azaindole or vehicle on both eyes, b.i.d., from day −1 to day 7 and day 13 to day 17. Again, intravitreal injection of Adv.SAA2 significantly increased mouse IOP from days 4 to 24 (vehicle group). Topical dosing of 4-azaindole significantly inhibited the Adv.SAA2-induced IOP during the period of treatment time (days −1 to 7 and days 13 to 17. 4-azaindole did not affect IOP in the non-injected eyes (FIG. 8A). Iris hyperemia was observed in all Ad.SAA2-injected eyes after day 4 and slowly decreased during the second week after injection (FIG. 8B). 4-azaindole did not affect hyperemia in the injected eyes, indicating the IOP-lowing effect of 4-azaindole was not through dispelling of iris hyperemia. These results demonstrate the potential of p38 MAPK inhibitors for treatment of ocular hypertension.

EXAMPLE 7

Recombinant SAA Decreased Outflow Facility in Perfusion Cultured Human Eyes

Figure 9:
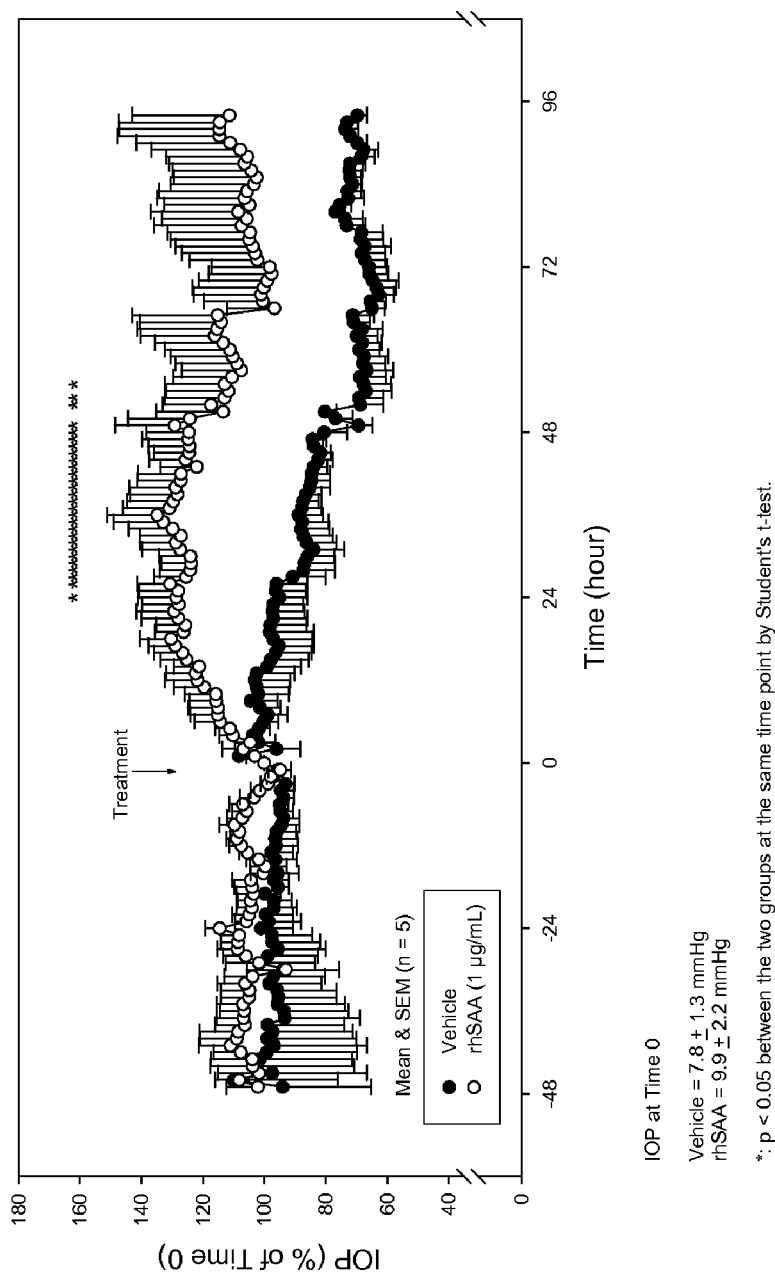
FIG. 9. Effect of recombinant human Serum Amyloid A (rhSAA, 1 μg/mL; treatment started at time 0) on IOP of perfused human anterior segments.
Figure 10:
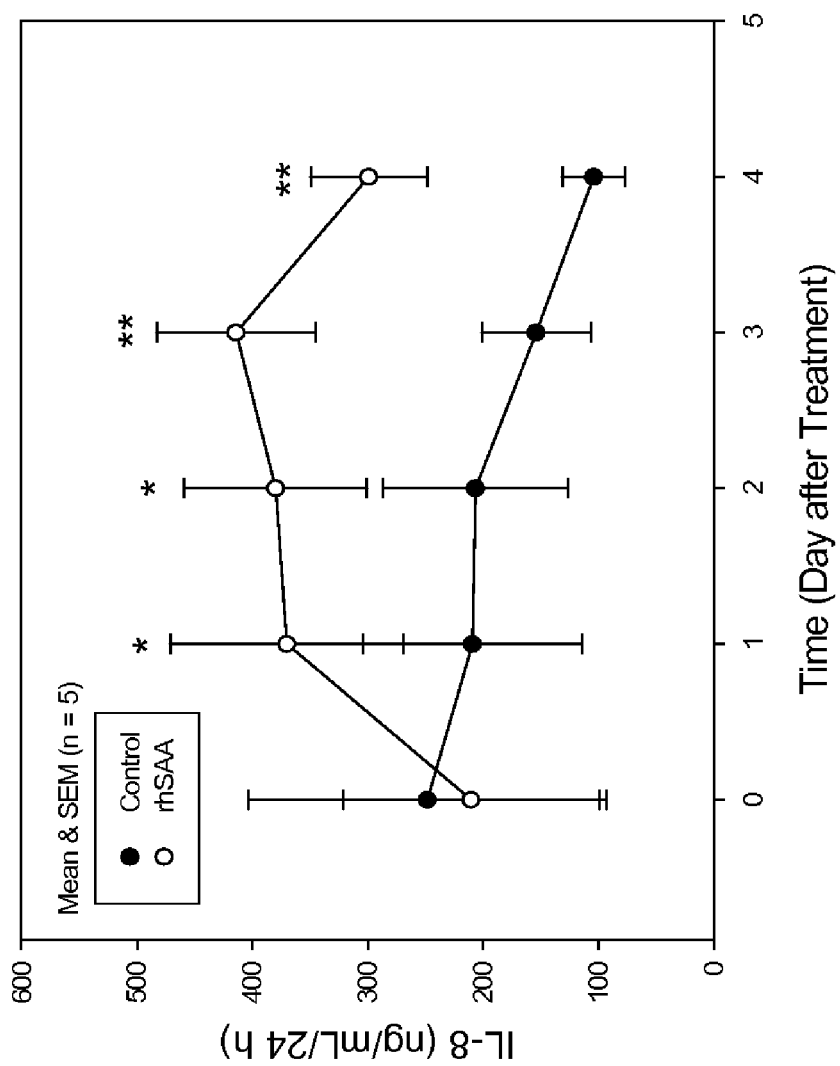
FIG. 10. Effect of recombinant human Serum Amyloid A (rhSAA, 1 μg/mL; treatment started at time 0) on interleukin-8 (IL-8) level in the perfusate of perfused human anterior segments.

Five pairs of human eyes were perfused with media containing either recombinant SAA (1 μg/mL) (experimental eye) or an equivalent volume of vehicle (control eye). At the end of the culture period, 4 quadrants of each eye were examined by transmission electron microscopy to determine TM tissue viability. Perfusate of each eye was collected and used for ELISA measurement of IL-8 level. All five had an elevated IOP within 24 h of treatment (FIG. 9). All five had an elevated IL-8 level (FIG. 10). The change in IOP correlated with SAA-induced increase in interleukin-8 in the perfusates. All five pairs of eyes had acceptable post-perfusion TM viability scores. These results demonstrated that increased SAA level can elevate IOP in perfusion cultured human eyes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

OTHER PUBLICATIONS

Furlenato, C J, and Campa A, *A novel function of serum amyloid A: a potent stimulus for the release of tumor necrosis factor-alpha, interleukin-1 beta, and interleukin-8 by human blood neutrophil*, BIOCHEM. BIOPHYS. RES. COMMUN 268:405-408 (2002).

He, R, Sang H, Ye, R D, *Serum amyloid A induces IL-8 secretion through a G protein-coupled receptor, FPRL1/LXA4R*, BLOOD 101:1572-1581 (2003).

Jensen L E and Whitehead A S, BIOCHEM. J. 334:489-503 (1998).

Jordat M S, et al., PLANTA MED. 68:667-71 (2002).

Kane et al., J. NEUROCHEM., 72: 1939-1947 (1999).

Kumon, Y., Hosokawa, T., Suehiro, T., Ideda, Y., Sipe, J. D., and Hashimoto, K., *Acute-phase, but not constitutive serum amyloid A (SAA) is chemotactic for cultured human aortic smooth muscle cells*, AMYLOID 9:237-241 (2002a).

Kumon, Y., Suehiro, T., Faulkes, D. J., Hosakawa, T., Ideda, Y., Woo, P., Sipe, J. D., and Hashimoto, K., *Transcriptional regulation of Serum Amyloid A1 gene expression in human aortic smooth muscle cells involves CCAAT/enhancer binding proteins (C/EBP) and is distinct from HepG2 cells*, SCAND. J. IMMUNOL. 56:504-511 (2002b).

Kumon, Y., Suehiro, T., Hashimoto, K., and Sipe, J. D., *Dexamethasone, but not IL-1 alone, upregulates acute-phase serum amyloid A gene expression and production by cultured human aortic smooth muscle cells*, SCAND J. IMMUNOL. 53:7-12 (2001).

Lambert et al., PROC. NAT. ACAD. SCI. USA 95: 6448-6453 (1998).

Liang, J. S., Sloane, J. A., Wells, J. M., Abraham, C. R., Fine, R. E., and Sipe, J. D., *Evidence for local production of acute phase response apolipoprotein serum amyloid A in Alzheimer's disease brain*, NEUROSCI. LETT. 225:73-76 (1997).

Liu et al., J. NEUROCHEM. 69: 2285-2293 (1997).

Miida T., Yamada, T., Yamadera, T., Ozaki, K., Inano, K., Okada, M., *Serum amyloid A protein generates pre-beta 1 high-density lipoprotein from alpha-migrating high-density lipoprotein*, BIOCHEM. 38(51):16958-16962 (1999).

Miller, *Genome Biology* 3(1):reviews 3001.1-3001.15 (2001).

Nakagami et al., EUR. J. PHARMACOL. 457: 11-17 (2002a).

Nakagami et al., BR. J. PHARMACOL., 137: 676-682 (2002b).

O'Hara, R., Murphy, E. P., Whitehead, A. S., FitzGerald, O., and Bresnihan, B., *Acute-phase serum amyloid A production by rheumatoid arthritis synovial tissue*, ARTHRITIS RES. 2:142-144 (2000).

Pike et al., J. NEUROSCI. 13: 1676-1687 (1993).

Thorn, C. F. and Whitehead, A. S., *Differential glucocorticoid enhancement of the cytokine-driven transcriptional activation of the human acute phase serum amyloid A genes, SAA1 and SAA*, J. IMMUNOL. 169:399-406 (2002).

Uhlar, C. M., and Whitehead, A. S., *Serum amyloid A, the major vertebrate acute-phase reactant*, EUR. J. BIOCHEM. 265:501-523 (1999).

Urieli-Shoval, S., Cohen, P., Eisenberg, S., and Matzner, Y., *Widespread expression of serum amyloid A in histologically normal human tissue. Predominant localization to the epithelium*, J. HISTOCHEM. CYTOCHEM. 46:1377-1384 (1998).

Yamazaki et al., BIOCHEMICAL AND BIOPHYSICAL RES. COMM., 290: 1114-1122 (2002).

Yankner et al., SCIENCE 250: 279-282 (1990)

Zhang et al., NEUROSCI. LETT. 312: 125-128 (2001)

---

We claim:

1. A method for lowering intraocular pressure in a patient suffering from elevated intraocular pressure, said method comprising administering to a patient in need thereof a therapeutically effective amount of a p38 MAPkinase inhibitor composition consisting of a small molecule agent that interacts with a gene encoding serum amyloid A protein (SAA), wherein said interaction modulates the expression of SAA, and wherein a decrease in expression of SAA lowers the intraocular pressure in a patient in need thereof.

2. The method of claim 1, wherein the agent is selected from the group consisting of 4-[4-(4-fluorophenyl)-5-(4-pyridinyl)-1H-imidazol-2-yl]phenol (SB202190), 4-(4-fluorophenyl)-2-(4-methylsulfinylphenyl)-5-(4-pyridyl)-1H-imidazole (SB203580), 5-(2-amino-4-pyrimidinyl)-4-(4-fluorophenyl)-1-(4-piperidinyl) imidazole (SB 220025), 4-(4-fluorophenyl)-2-(4-nitrophenyl)-5-(4-pyridyl)-1H-imidazole (PD 169316), trans-4-[4-(4-fluorophenyl)-5-(2-methoxy-4-pyrimidinyl)-1H-imidazol-1-yl) cyclohexanol (SB 23063), 3-(4-fluorophenyl)-2-(pyridin-4-yl)-1H-pyrrolo[3,2-b] pyridine, 1-(5-tert-butyl-2-p-tolyl-2H-pyrazol-3yl)-3(4-(2-morpholin-4-yl-ethoxy) napthalene-1-yl)urea (BIRB-796), and 2-(4-chlorophenyl)-4-(4-fluorophenyl)-5-pyridin-4-yl-1, 2-dihydropyrazol-3-one (CalBio506126).

* * * * *

UNITED STATES PATENT AND TRADEMARK OFFICE
CERTIFICATE OF CORRECTION

PATENT NO. : 7,662,389 B2 Page 1 of 1
APPLICATION NO. : 11/615454
DATED : February 16, 2010
INVENTOR(S) : Clark et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this

Thirtieth Day of November, 2010

David J. Kappos
*Director of the United States Patent and Trademark Office*

SEQUENCE LISTING

```
<160> NUMBER OF SEQ ID NOS: 13

<210> SEQ ID NO 1
<211> LENGTH: 369
<212> TYPE: DNA
<213> ORGANISM: homo sapiens

<400> SEQUENCE: 1
atgaagcttc tcacgggcct ggttttctgc tccttggtcc tgggtgtcag cagccgaagc      60
ttcttttcgt tccttggcga ggcttttgat ggggctcggg acatgtggag agcctactct     120
gacatgagag aagccaatta catcggctca gacaaatact tccatgctcg ggggaactat     180
gatgctgcca aaagggggacc tgggggtgtc tgggctgcag aagcgatcag cgatgccaga     240
gagaatatcc agagattctt tggccatggt gcggaggact cgctggctga tcaggctgcc     300
aatgaatggg gcaggagtgg caaagacccc aatcacttcc gacctgctgg cctgcctgag     360
aaatactga                                                            369

<210> SEQ ID NO 2
<211> LENGTH: 122
<212> TYPE: PRT
<213> ORGANISM: homo sapiens

<400> SEQUENCE: 2

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
                20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
```

```
            50                  55                  60
Arg Gly Pro Gly Gly Val Trp Ala Ala Glu Ala Ile Ser Asp Ala Arg
 65                  70                  75                  80

Glu Asn Ile Gln Arg Phe Phe Gly His Gly Ala Glu Asp Ser Leu Ala
                     85                  90                  95

Asp Gln Ala Ala Asn Glu Trp Gly Arg Ser Gly Lys Asp Pro Asn His
                100                 105                 110

Phe Arg Pro Ala Gly Leu Pro Glu Lys Tyr
                115                 120
```

<210> SEQ ID NO 3
<211> LENGTH: 570
<212> TYPE: DNA
<213> ORGANISM: homo sapiens

<400> SEQUENCE: 3

```
agggacccgc agctcagcta cagcacagat cagcaccatg aagcttctca cgggcctggt      60
tttctgctcc ttggtcctga gtgtcagcag ccgaagcttc ttttcgttcc ttggcgaggc     120
ttttgatggg gctcgggaca tgtggagagc ctactctgac atgagagaag ccaattacat     180
cggctcagac aaatacttcc atgctcgggg gaactatgat gctgccaaaa ggggacctgg     240
gggtgcctgg gccgcagaag tgatcagcaa tgccagagag aatatccaga gactcacagg     300
ccatggtgcg gaggactcgc tggccgatca ggctgccaat aaatggggca ggagtggcag     360
agaccccaat cacttccgac tgctggcct gcctgagaaa tactgagctt cctcttcact      420
ctgctctcag gagacctggc tatgaggccc tcggggcagg gatacaaagt tagtgaggtc     480
tatgtccaga gaagctgaga tatggcatat aataggcatc taataaatgc ttaagaggtc     540
aaaaaaaaaa aaaaaaaaaa aaaaaaaaaa                                      570
```

<210> SEQ ID NO 4
<211> LENGTH: 122
<212> TYPE: PRT
<213> ORGANISM: homo sapiens

<400> SEQUENCE: 4

```
Met Lys Leu Leu Thr Gly Leu Val Phe Cys Ser Leu Val Leu Ser Val
 1               5                  10                  15

Ser Ser Arg Ser Phe Phe Ser Phe Leu Gly Glu Ala Phe Asp Gly Ala
                20                  25                  30

Arg Asp Met Trp Arg Ala Tyr Ser Asp Met Arg Glu Ala Asn Tyr Ile
             35                  40                  45

Gly Ser Asp Lys Tyr Phe His Ala Arg Gly Asn Tyr Asp Ala Ala Lys
     50                  55                  60

Arg Gly Pro Gly Gly Ala Trp Ala Ala Glu Val Ile Ser Asn Ala Arg
 65                  70                  75                  80

Glu Asn Ile Gln Arg Leu Thr Gly His Gly Ala Glu Asp Ser Leu Ala
                 85                  90                  95

Asp Gln Ala Ala Asn Lys Trp Gly Arg Ser Gly Arg Asp Pro Asn His
                100                 105                 110

Phe Arg Pro Ala Gly Leu Pro Glu Lys Tyr
                115                 120
```

<210> SEQ ID NO 5
<211> LENGTH: 4286
<212> TYPE: DNA
<213> ORGANISM: homo sapiens

<400> SEQUENCE: 5

```
gatggttgac aactcccctc ctcttccccc tcttctactg tctactcctg ggaccaagtg      60
agccacgcca gctcagatac tacactgacc acagggaatc ccaccttttc caaggaatgg     120
aagttgtgta gggaatattc aaatgttgct tagcattgcc ttagataaga accaaaggga     180
cagggaaatc ctctgacagc tatctgcctt ataactttca ttttactgtg cctaaaatat     240
gctcagaacc cagaaagagg cataattcct aattttggca ggctctaatc taaaataatg     300
attctcaaac atggtgtgac ttttgtctat ttgctttatc ctgggtcact gctcctcttc     360
tgtcagatac tgggattcca atgagacaaa tggaaatgga gacgtagacc ctctgacctt     420
ctatctttta tctatacaca tacacctgtg tgtgtgtgtg tgtgtgtgtg tgtgcgtgtg     480
taaaaccgag tgggttttttt tcttggaatg aaagaatgga ctaacattac aaaaaataaa     540
aacttgaaac agaatgtgta ttatccttgg ttgtgtttcc ttggccctgc agcaggatga     600
agctctccac tggcatcatt ttctgctccc tggtcctggg tgtcagcagc caaggatggt     660
taacattcct caaggcagct ggccaaggtg aggtccacag gataggggc aggaggctgc      720
ttctggctgc ccccaggatg cagctgagca gaggccacat ccccactggg caaaggtgct     780
agtgatgcca cagatggata gagaaggggc atgttttttc ataagcgtgg ttcctcatgc     840
ttttctggac agctttgaca ctcttctatg aggatcctcc agccgaggtc gcataaggtg     900
tgagctgcct cttttcagca ggaccatgag agagatgtgg agttgagggg tgcatgttcc     960
cataataccg gtgggctct actgccccct agtgggaaat ctgggacagt tcatgtctat    1020
gtctcctggg aagccaggaa gcaggtggat caaaagtgtg aggcgagtcc atggggaagc    1080
tgaacggagc caaccgtccc cataaaaaca accaagctta gctgagattt taatacgtac    1140
taggcactgt ttaaatgtac taatgaattg gtttccatca tttagtccta tgatgcaagc    1200
agcattatcc cttaacagag aagctaacac acacacacac acacacacac taacacacac    1260
acacacacac acacacacac aaaccccaag atacgtaaag aagttccaaa gcagagcagg    1320
attaacccag gcagtcttgc tctgcagaac ttgctcttaa tcaaggtact ctgctgcttt    1380
caaaacaaga gtttcggatt tgtgaacaca tagctcatcc tttatctaag aaatggcaaa    1440
taggatgtgt tgccttttgga aggtaagtct agctccactt atcccagtaa aacctacagt    1500
gaattacctt gatggtggtt ctactggggc ttatatatgg ccaggaaact gctagcaaga    1560
gaaatatacc ccgagggctg gcacagtgg ctcacacctg taatcccagc actttgggag     1620
gctgaggtgg gcagatcacc tgaggtcaag agttcgagac cagcctggcc aacatggcga    1680
aatcctgtct ctactaaaaa tacagaaatt agccgggtgt ggtggcatgc gcctataatc    1740
ccagcctctc gggaggctga gggagaagaa ttgcttgaac tcaggaggca gaggttgcag    1800
tgagctgtga tcacaccact gcactccagc ctaggagaca gagcaagact ccatctagag    1860
agacagagag agagagagag ggagaaatat accccactag ccataataaa gtggcaaaat    1920
tttgttttca gaatgcagta ttttaaattt caggtattat tatttttctg agtctctgaa    1980
aaatggtttt aaggatttgc ttttaatcct atttacatgt tcacacactc aactacaaat    2040
atctttcatt ccttaggtta atattttca aaggggttgtt ctgggaccac ttgcgtgaga    2100
atcacctgga ttctgggatg ctttgtgaaa tgaaatgaag attcccgggt ccatacccta    2160
cccccctgccc ccaacagcca cagtctcttg ggacagagcc tagaaatctt gccttttgcta   2220
agcacctcgg tagattttta tgcacagcaa aggttgagaa ccactacctc ttgttttgct    2280
```

```
gctgaaagtg ataaaatgtg ccaggaattt tggaagtact tattaagcca atctgaacat    2340
caaggagcca tttaagtcag taactcagag gaataagtag agtaaaaatg tcataaactc    2400
tcaataaaag caatcaattt aacaccagga gtaataaatg cataaaatga agatgagtta    2460
tctaatagag aaattatata aaccatgatt ataactctat atttgagttc cccctttttcc   2520 gtaatcagtt aattttctaa aaaatcttcg tcacttaatt ctagcttgat cagatccctt    2580
cagtccgtaa ctccctgctc ctcatcttag tttagcccctt cttttttctt atgccaccttt  2640 tcctaaggac cagagaagtg aaatgataat atattggcca cctacaatgt tctagacatc    2700
atacatgtat tttctctgct cttctgcata atcactgtga ggcaggcaat actcctccat    2760
ttcattgggg aggacattga ggttctgaac tagtgggtca gttgtccttt ttctgaattt    2820
gattacccag tagtataaag ctttcttagg taactcacct ttatcacttg ctgactgaat    2880
tctgacagat gtcagtttct aattatagcc tggacattca gatgtattca ggaccaagtt   2940
gtcctcactc tacctacagg catgaatttc tctcattgac taggttagga gcgccatatg   3000
tctgcagcct ccctcagaat cccctgtgtt ctcacaccag ggaactgagg gttccctggg   3060
tccttccagg tagaagttca ttgtacaatg aaacatccct taaggaccat ttcatctctt   3120
ctttaggtgc atcacacatg gttaaaacaa agtaataaca gaacttagaa tggaatcaaa    3180
cagaatgaaa cttacaccaa gtacaattct cattacatta acccagaaaa gtgaaaagta   3240
gaagaatatt tatttcaagc caatataatt tccaagggct ttgttgaagg ctgaaatctt   3300
cgggaggaaa gtagtgagaa gaaaactgtt cattcctcta ttttcccagt atataattgt   3360
tttgatcatt ttcttttcctt tccagggact aaagacatgt ggaaagccta ctctgacatg   3420
aaagaagcca attacaaaaa attcagacaa atacttccat gcttgggggg actatgatgc   3480
tgtacaaagg gggcttgggg ctgtctgggc tacagaagtg atcaggtaat gcacattcct   3540
gatgttgcca ggaatgagtg agcagagctt gactgccttg gacagtcagg agagaggtaa   3600
gctccttgca gagaagttag aggctgcagc ccctcctcct cttgccctct ctctgcctgt    3660
gtgcttagtg cgagggtctg agtggatggt agaagtgagt gattcctcac cctccctctc   3720
tgggtgctgt tcatccagcc tagggtgcc cagcctggct gagtggggca gtgcccaggc    3780
agggtcattg ttttcacccc tccttccttg gccttcctgg gcttctccca gagtcctccc   3840
ttggaaagca gagaatggga aggtgggctg ttgctcactg gcctggtgat taatctcctt    3900
gcttgcctgg actacagcga tgccagagag aacgtccaga gactcacagg agaccatgca   3960
gaggattcgc tggctggcca ggctaccaac aaatggggcc agagtggcaa agaccccaat   4020
cacttccgac ctgctggcct gccagagaaa tactgagctt ccttttcaat ctgctctcag   4080
gagacctggc tgtgagcccc tgagggcagg gacatttgtt gacctacagt tactgaattc    4140
tatatcccta gtacttgata tagaacacat aaaaatgctt aataaatgct tgtgaaatcc   4200
agtttgttat tggaatctgg aagcagaata tgacagtcct cctgggatca tgggcctgtt   4260
tagtaccata gggatgacca ataaac                                         4286

<210> SEQ ID NO 6
<211> LENGTH: 193
<212> TYPE: DNA
<213> ORGANISM: homo sapiens

<400> SEQUENCE: 6
gttttctgct ccttggtcct gggtgtcagc agccgaagct tctttcgtt ccttggcgag       60 gcttttgatg gggctcggga catgtggaga gcctactctg acatgagaga agccaattac     120
```

```
atcggctcag acaaatactt ccatgctcgg gggaactatg atgctgccaa aagggggacct    180 gggggtctgg gct                                                        193
```

```
<210> SEQ ID NO 7
<211> LENGTH: 64
<212> TYPE: PRT
<213> ORGANISM: homo sapiens

<400> SEQUENCE: 7
```

```
Val Phe Cys Ser Leu Val Leu Gly Val Ser Ser Arg Ser Phe Phe Ser
1               5                   10                  15

Phe Leu Gly Glu Ala Phe Asp Gly Ala Arg Asp Met Trp Arg Ala Tyr
            20                  25                  30

Ser Asp Met Arg Glu Ala Asn Tyr Ile Gly Ser Asp Lys Tyr Phe His
        35                  40                  45

Ala Arg Gly Asn Tyr Asp Ala Ala Lys Arg Gly Pro Gly Gly Leu Gly
    50                  55                  60
```

```
<210> SEQ ID NO 8
<211> LENGTH: 369
<212> TYPE: DNA
<213> ORGANISM: homo sapiens

<400> SEQUENCE: 8
```

```
atgaagcttc tcacgggcct ggttttctgc tccttggtcc tgagtgtcag cagccgaagc     60 ttctttttcgt tccttggcga ggcttttgat ggggctcggg acatgtggag agcctactct    120
gacatgagag aagccaatta catcggctca gacaaatact tccatgctcg ggggaactat    180
gatgctgcca aaggggggacc tggggggtgcc tgggccgcag aagtgatcag caatgccaga    240
gagaatatcc agagactcac aggccatggt gcggaggact cgctggccga tcaggctgcc    300 aataatggg gcaggagtgg cagagacccc aatcacttcc gacctgctgg cctgcctgag     360
aaatactga                                                            369
```

```
<210> SEQ ID NO 9
<211> LENGTH: 122
<212> TYPE: PRT
<213> ORGANISM: homo sapiens

<400> SEQUENCE: 9
```

```
Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120
```

<210> SEQ ID NO 10
<211> LENGTH: 369
<212> TYPE: DNA
<213> ORGANISM: homo sapiens

<400> SEQUENCE: 10

| | | |
|---|---|---|
| atgaagcttc tcacgggcct ggttttctgc tccttggtcc tgagtgtcag cagccgaagc | 60 |
| ttctttttcgt tccttggcga ggcttttgat ggggctcggg acatgtggag agcctactct | 120 |
| gacatgagag aagccaatta catcggctca gacaaatact ccatgctcg ggggaactat | 180 |
| gatgctgcca aaaggggacc tggggggtgcc tgggccgcag aagtgatcag caatgccaga | 240 |
| gagaatatcc agagactcac aggccgtggt gcggaggact cgctggccga tcaggctgcc | 300 |
| aataaatggg gcaggagtgg cagagacccc aatcacttcc gacctgctgg cctgcctgag | 360 |
| aaatactga | 369 |

<210> SEQ ID NO 11
<211> LENGTH: 122
<212> TYPE: PRT
<213> ORGANISM: homo sapiens

<400> SEQUENCE: 11

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly Arg Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 12
<211> LENGTH: 10001
<212> TYPE: DNA
<213> ORGANISM: homo sapiens

<400> SEQUENCE: 12

| | | |
|---|---|---|
| gggtggatca cgaggtcagg agatcgagac catcttggct aacatggtga aaccccgtct | 60 |
| ctactaaaaa tacaaaaaaa ttagccgggc gtcatggtgg cgcctgtag tcccagctac | 120 |
| tcgggaggct gaggcaggag aatggtgtga acccgggagg cagaacttgc agtgagccta | 180 |
| gatcgcgcca ctgcactcca gcctggggga caaaacgaga ctctgtctca aaaaaaaaaa | 240 |
| aaaaaattcc cacattagag ttggggaaat gggcagtcct ggtggaagtt agggaacaga | 300 |
| tctgggacac gttatagcca gctggactac aggaggccat aagctcaatt cttccttgac | 360 |
| tctgaaacct tccactggtc ctaatgccta gtaattccag gccttccca gttgtgccag | 420 |
| gcttggaggt gaacacatct atgtgccaag aaggaaaggt atgccaagca ggggcttaag | 480 |
| tcatccttat cctcagtctg tctatgagtg gtatgtaccc ctgttcccct tgcaagatct | 540 |

```
gctgggctta ggtctcctgg ctgtgagttc cccatacctg ggcataaatg tagtgagcct      600
gagctcccaa ataaggttgg gggctccaga gaggtggaga gccctgtgtc tgggaagtgt      660
gcccacccag caggtctgac caggaagata cactgctagg gttatggaaa aagactatgt      720
gtcaaggtct cttgattctc catctaggca gagaatcatc tttaattaat gggaaactgg      780
aaggcaaatt acttggacct gaaattactt tttgtttatt gaaccactgt gttgtaaatc      840
acatctctct gaaggcaaga gaaatcaggg agttacaaaa tgtttaggag aactaaacag      900
gactccctgt tttgctaact aatcagattg agacaggctc tctggtaaat ctacaaattt      960
gatgttgttc aaccataagc agtaaatttc ctatgctgga ttttcctgac aatgaatgta     1020
aaaggaaaag gagtcttttt gacaaaatat tttattgttc atctaaactg aaaaacttct     1080
ctattttttca aaattgctat acgtgtttaa agatgtagat atttgaatag cctaactggt     1140
acagaaggtt taatgatgat tcctaagaca tacctataaa ttacttgaaa ttgaaacgaa     1200
atttaagaag aattattgga attttcccct tctcaaatga gttcttagtt tcataaatac     1260
tatacaagtc cataagagat ttggggtttt gagatgtctt ttttttttttt ttttttttcag     1320
acggagtttc actgttgttg cctaggctgg agtgcaatgg cgtgacctca gctcactaca     1380
acctccacct cccaggttca gcgattttc ctgcctcagc ctcccaagta gctgggatta     1440
cagggacctg ccacaacgcc aagctaatgt tttgtatttt tagtagagat ggggttcacc     1500
atgttggcca ggcttgtctg gaactcctga cctcaggtga tccacccgcc tataatttat     1560
tactcccttt tgcaaatgtt tgaaaaggaa taaagtgcaa tattttttaaa cagaatgcag     1620
agttctgttg tccttttggca ataccagttt cagactctga gagtggctct tgctgttgcc     1680
gacagtgggc tgatgaccaa atcccaacat gcccccgctg cgagtccttc ataacctgat     1740
tcagtcatca cttagaggcc agcaggcttc agggaggcgt gagcctcagc caacaaccta     1800
taggggaaga gacgcagaac tcaatgcaga caggtttgga ttctggtgcc tagagaatgc     1860
aacttggaaa ctctgagcca ggagaaaagg gttctctctc catgagagag tgtgggcttt     1920
gtgagaagcg acacacagca aacacaatta agagtccacc cctcagcggg gcgcaggggc     1980
tcacgcctgt aatcccagca ctttgggagg ccgaggcggg tggatcacga ggtcaggaga     2040
tcaagaccat cctggctaac acagtgaaac cctgtctcta ctaaaaatac aaaaaaatta     2100
gccgggcgtg gtggcgggcg cctgtggtcc cagctactcg ggaggctgag gcaggagaat     2160
ggtgtgaacc cggagggtgg agcttgcagt gagccgagat cgcgccactg cactccagcc     2220
tgggcgacag agcgagactc catctcaaaa aaaaaaagaa aaagaaaaag aaaaagagtc     2280
cgccctgaa ttaaatagtt ggtccttttg tgttcctggt gattcacttg ctaagtggaa      2340
gaaacaggag ggaatctttt ctcctgccct cctggtaatc catagcccat ggcctggctt     2400
tacttctgta aagtggcagg agaccttttg acagctgagc catttcttat tttatttatt     2460
ttaataagag atggtaggaa tgagcaatga tattagtacc tggggactgt tgttcttaag     2520
gagaaacaat cttagaatga ttagtgatac cccttgcttt ctcttttctt tcattatact     2580
ttttgtacac atatttttcc catttattta ttggaatctt actgatttat tataagtata     2640
agctttatgt ctacacatgt ataatcattt ttccccaagt ataagtctct ttttcatgga     2700
ggcacagcct agacctggtt agccgccatc tcccctcatt gtatgcccaa tatctattgt     2760
agtatctgct gcatagaagg cactcgatgc gtgaatggat aatgactgat gatgaatcaa     2820
taaataaatg gacatgtcat tgtaaaaaat tctaaaaatc tagaataaca caagctgttg     2880
```

```
gcactaccta gaaacacaga tgtaaaactt cctaggttgt gtttcaccat gggaacatgt    2940
ctttgaacaa aaatgggatc atattctatt gcactctttc ccttaagaga tacttctcca    3000
ggtcattaag tgctcttcca caatatcagt atatggcaga ggcaaggtca taccaggtct    3060
gtctgaaacc agggcttggc tcttaacttg cagccatact gcctccaagt ctaggtggct    3120
gggttttagg atctgtaatg ggaactcagt gtcacaacct ctactgggaa ggtattctgg    3180
tgttgcataa caggactttc tgttagagat aaccatggca aaatgaaata gagacaaagt    3240
tcaggtttct gctgccagga gctgagattg ctgtgaccaa tggcattctc ccaaaccaaa    3300
taatccaacc tggaattacc ataaaccact cctcatcttt tcaaggggtg tccaagttcc    3360
cagaaaagaa catttgttaa gggatggagg caaggaggtg gagaagaaag agcactggcc    3420
aaggtatcat gagtgtcctg ggttctggtc cttgaataag ccatttatct tctctgcagc    3480
ttctccatct gataggagtt tggaggcaga gttttttctt aatgagcaaa agacagtcgt    3540
gcctaggaga tgtggtgtac atgttagaaa gaagggactg gctgtgactc tataaaagat    3600
gaattcatac aaaaacaaat tacccttttcc cagggagaaa gtttggatcc agtaattaga    3660
gatctcaaaa agtagaagac ctgccctgtg aggcctgtgg cctccaagtt tgaatgctgt    3720
gtgtcagctt taaaaactag tttcttgctg ataaatgttt catattaagc atgtgttgag    3780
agtactcctt gcctaccttc actagccact gtttccttcc cctcctccct tgtcccttca    3840
ttctctccag aactttctgc taacttccat tctcttcagg acttcagcat ggttgggaga    3900
agatcagaaa ggcatcctca ctgttttttat tttagtccac ttgacctttg gggagtagtt    3960
ccactggctc ataagtatca gccccccata gcacagcacc ccacactgag cccggaagca    4020
ataaagaatc ccaatctgct gtcactaacc agcacgctca actgccatgc cctttactct    4080
tctcatctcc ctgctttcac gtcacaccaa ctaatttctc tatgagtcag cctcaactct    4140
cccaacactc tgcccaccct tcttctacta cccttccagtg agctcctcga aagaagggtc    4200
tgcggtgagg atgcccccttt atctctgcct atttccttcc cattacaaaa acttgaaacc    4260
tgcctttccc atgttgattt cactttattc tcatctttac ccatggggta tgcctcctgc    4320
aattcctcct agacaataga atgagaaaga ggggtcctcg tcctctttgc tttccatgac    4380
catttctcca ttcttcacct ctgtgatgtg tcctctttga agtccctgat aaattcatta    4440
ccaccttctc tccagtctta ctaatgttat ctgcacaagt gatttccaaa caggaagatt    4500
ttcaaacact gattcctgaa gatcaccccc aactcgctga actgagacca agacctccaa    4560
gattatggct taggaatctg catttttttt ttttttttga gacaagagtc tcgctctgtt    4620
gccaggctag agtgcaatgg tggaatcata gctcattgta acctcaaaact cctgggctca    4680 agtgatcttc ctgcctcagc ctcccaagta gtgaggacaa caggagtgtg ccaccatgcc    4740
cagctaattg ttaattttttt gtagaaatgg agtctcacta tgttgctcgg gctggtctca    4800
aactcctgac cttaacccat cctccgcctc cgccccaaaa agtgttggga ttacaggtgt    4860
gagccaccgt gcccagccta gaaatacccca ctagaagctt ctgtgtagac aatctgctta    4920
gtgatgtttg gagacaaagt acctctttat tgtattcatt gacaaaactc tccagtcctc    4980
tcccatcttc atggaaaatt ttcacagttc atttacggcc ctctttccaa cacattcact    5040
gccaatactc ttattgacaa taactgtatt gttgaacctt ccagtatcct gcattcccgg    5100
atcaaggccc cctcaaagcc ctgatatgca aatatctggg aaaagaatgt tccagaggaa    5160
aggaacagct aatccgaggc ccctagggta agatgtgcct gggggtttgg agaccagtgt    5220
ggccagagca aaatgagcag gaggagagaa ttggatgatg aggtacgaga ggaaggagtt    5280
```

```
aggacagttt gagtaaagtt tgaaaaccat tataagggct ttgacttcaa ctatgagtgg    5340
aagtggaatc ctccggagag ttttgaatgg agagtgatag aagttgtctt gtgttgtaac    5400
agtctggctg ctatactgaa aagagactag ttggcggcaa aggggaaat gtggaagcca    5460 gttaagaagc catcataacc cagaaggtga tgcctaataa catctctctg ggagcagcgg    5520
agagatgata agggtttgcc ttctgaatat gttttttgac aattaatgta aacatttcaa    5580
gtaggctgag attttattgc atattaacaa tgtccatgtt cactcgcggc agccgccccc    5640
ttctgcgcgg tcatgccgag ccagcacctg ggcctggaac tgggccgcag cccccagctt    5700
cacccaccac ctccctacca tggacccctg caaagtgaac gagcttcggg cctttgtgaa    5760
aatgtgtaag caggatccga gcgttctgca caccgaggaa atgcgcttcc tgagagagtg    5820
ggtggagagc atgggaggta agtaccacc tgctactcag aaggctaaat cagaagaaaa    5880
taccaaggaa gaaaaacctg atagtaagaa ggtggaggaa gacttaaagg cagacgaacc    5940
atcaactgag gaaagtgatc tagaaattga taaagaaggt gtgattgaac cagacactga    6000
tgctcctcaa gaaatgggag atgaaaatgt ggagataacg gaggagatga tggatcaggc    6060
aaatgataaa aagtggctg ctattgaagt cctaaatgat ggtgaactcc agaaagccat    6120
tgacttattc acagatgcca tcaagctgaa tcctcgcttg gccattttgt atgcaaagag    6180
ggccagtgtc ttcgtcaaat tacagaagcc aaatgctgcc atccaagact gtgacagagc    6240
cattgaaata aatcctgatt cagctcagcc ttacaagtgg cggggaaag cacacagact    6300 tctaggccac tgggaagaag cagcccatga tcttgccttt gcctgtaaat tggattatga    6360
tgaagatgct agtgcaatgc tgaaagaagt tcaacctagg gcacagaaaa ttgcagaaca    6420
ttggagaaag tatgagcgaa aacatgaaga gcgagagatc aaagaaagaa tagaacgagt    6480
taagaaggct caagaagagc aggagagagc ccagagggag gaagaagcca gacgacagtc    6540
aggagctcac tatggccctt ttccaggtgg ctttcctggt ggaatgcctg gtaattttcc    6600
cggaggaatg cctggaatgg gaggggacat gcctggaatg gccggaatgc tggactcaa    6660 tgaaattctt agtgatccag aggctcttgc agccatgcag gatccagaag ttatggtggc    6720
cttccaggat gtggctcaga acccagcaaa tatgtcaaaa taccagagca acccaaaggt    6780
tatgaatctc atcagtaaat tgtcagccaa atttggaggt caagcataat gcccttctga    6840
taaataaagc cctgctgaag gaaaagcaac ctagatcacc ttatggatgt cgcaataata    6900
caaaccaacg tacctctgac cttctcatca agagagctgg ggtgctttga agataatccc    6960 taccctctc ccccaaatgc agctgaagca ttttacagtg gtttgccatt agggtattca    7020
ttcagataat gttttcctac taggaattac aaactttaaa cacttttaa atcttcaaat    7080 atttaaaaca aatttaaagg gtctgttaat tcttatattt ttctttacta atcattgtgg    7140 attttttcctt aaattattgg gcagggaata tacttattta tggaagatta ctgctctaat    7200
ttgagtgaaa taaaagttat tagtgcgagg caaacataaa aaaaaaagt ccatgttcat    7260 ctctaaatga catcattgtt ccaaagcttt tccattcttc ttaaccttcc acctgtcaat    7320
ctataggaga tgacttctcc tacttcactc atgcattgac tccttcaatc aataaaagtg    7380
actaagaacc tgctacaggt gaggtgctgt gtttggtgtt aaagtgacaa cagttatctg    7440
tcaataagcc tgacaaggtt cctatccctg tgttttgtgc actctgggtc aaactcagaa    7500
atgcaaacag gtgagagcg atgagttcta tgactggtaa agaaagggc ctgctggttt    7560 ccctcaggat ctctgtcctt catctcaaaa tgcatcttcc ttgttatcgt tcctctcctt    7620
```

```
cctgtctcag aggaagacct gctcctgcta cactctgggc aaccttgtcc ccgtggccct    7680
gtggcccctt ggttgttgaa gtctatgtta tgccctatct tttaccctca gtcactctct    7740
ctgttaacat tctccctgtg ccctgtaacc ctccctcatc tttaaataaa tcctcctcct    7800
ttgaccttcg catgtattca gtcatgcaac tcaacaagca tttattgcac agtgatattc    7860
aatttgccac ttgctaaaag tctgaacctt ggcagctgaa tgtgatcaga aaaaaagcac    7920
gactgctatg actagtctca ctttaaattc atggtcgttg accaagagct accatacaat    7980
ccactacctt tctcaagttc agtcacattc ttcctttcct agatgtctgc tttctacttc    8040
tcttctcttc tgaaacttcc cacaactcct cgttcattct cttctcagtt gacaactttg    8100
cttcctattt cactgaaaaa tagaagcaat cagatatgaa cttctggctg gcatggtag    8160
ctcatgccta taatctcagc actttgggag gccaaggcag gaggactgca ggttaggaat    8220
ttgagaccag cctgggcaac atggtgaaac tcccactgta ctaaaaattt taaaaattac    8280
tcaaacatat tggcaaacaa ctgcagtccc agctacttgg gaggttgaga tgcaaggatc    8340
acttaaacct gggaggctga ggctgcagtg agccatgatt gcaccactgc actccagctc    8400
aggcaacaga gcaagaccct gtcttgagag gagaggagaa gagaggaggg gaggggaggg    8460
caggggaggg gaggggaggg gaagggagag gggaggggag aggggaggag agaggggagg    8520
ggaggggagg ggaggggagg ggaggagagg aggatcaggt gaggagtatg ccaaggagtg    8580
tttttaagac ttactgtttt ctctttccca acaagattgt catttccttt aaaaagtagt    8640
tatcctgagg cctatattca tagcattctg aaagaaagaa aagaaaagag gaaagaaaga    8700
gagaggaagg aaggaaggag aaagagagag gaaggaagga gaaagagaga ggaaggaagg    8760
gaggaagaga agaagggagg aagaaaagaa ggaaggaagg agggagggag ggaagggagg    8820
gagggaaaga ggaagaaagg agggaaagaa ggaaggaaga gagagaggaa ggaaggagga    8880
agagagaaga aggaaggagg aagacagaga gggagtaagg aaggaaggaa ggagaaaagag    8940
agaggaagga agaaatgaag gaaggaagga aagaaagaaa aaataaaaga gtgaaaacgg    9000
actggagaag aagaaaccac agttgctgct atatccacca gcctctctgc atgtcctggc    9060
ctcagccctg ctgggctctg gtactgacca cttccttcct tcctaatttc ctaattgact    9120
aggccagctg agcagggctt ttctgtgctg aggaggtaaa tctctggata tctagactga    9180
ggggtggaag gagccttcca gggcacacat gagacatggc aggggtaggc tgctagtttt    9240
attttgtttt cttttagaca cagggtcttg ctctgttaac caggctggag tgcagtggcg    9300
tgattatagc tcactgcagc cttgacctcc tgggtctccc acaatcctcc cgcttcagcc    9360
tcttgagtag ctgggactgc aggtgcacac taccacaccc ggtccattta ttttttatatt    9420
tcgtagagac aagatcttac agttttgcac agagtgatct taaactcttg accccaagtg    9480
atcctcctgc cttggcctcc aaaagcattg ggattatagg agtgagccac tgtgctggac    9540
ctagtctgtc agctttgaag ctttagatat gaactcagag ggacttcatt tcagaggcat    9600
ctgccatgtg gcccagcaga gcccatcctg aggaaatgac tggtagagtc aggagctggc    9660
ttcaaagctg ccctcacttc acaccttcca gcagcccagg tgccgccatc acggggctcc    9720
cactctcaac tccgcagcct cagccccctc aatgctgagg agcagagctg gtctcctgcc    9780
ctgacagctg ccaggcacat cttgttccct caggttgcac aactgggata aatgacccgg    9840
gatgaagaaa ccactggcat ccaggaactt gtcttagacc gttttgtagg ggaaatgacc    9900
tgcagggact ttccccaggg accacatcca gcttttcttc gctcccaaga aaccagcagg    9960
gaaggctcag tataaatagc agccaccgct ccctggcagg c                     10001
```

<210> SEQ ID NO 13
<211> LENGTH: 10001
<212> TYPE: DNA
<213> ORGANISM: homo sapiens

<400> SEQUENCE: 13

| | | | | | |
|---|---|---|---|---|---|
| gtctgccagg | gagaggtggc | tgctatttat | agtgagcctt | gctggtctct | tgggagggaa | 60 |
| gaaaagctgg | atgtggtccc | tggggaaagt | ccctgcaggt | catttcccct | acaaactggt | 120 |
| ctaagacaag | ttcctggatg | ccggtggttt | cttcatcccg | ggtcatttat | cccagttgtg | 180 |
| taacctatgg | gaacaagaga | ggtttgctgt | gccttggcaa | tggacagggt | gctagatcag | 240 |
| ctctgctcct | cagcattggg | ggaagtgcag | ctgcagagat | gccagtggga | gccccgtgat | 300 |
| ggcggcacct | gggctgctgg | aaggtgtgga | gtgagggcag | ctcttcagcc | agctcctgac | 360 |
| tataccggtc | atttcctcag | gatgggccct | gctgggccac | atggcagatg | accctgactg | 420 |
| aaatccctgt | gagttcatgt | ctaaagcttt | aagctttaaa | acggacagcc | taccccctgcc | 480 |
| acatctcatg | tgtgccctgg | aagcctcctt | ccaccctct | ggatgtcctg | atatttctca | 540 |
| gcacagaaaa | tctctgctcc | gctggcttag | ccaatttgga | aatgcttttt | ctaagttggc | 600 |
| tcctgagcca | aggacaatgt | agagagggg | actttctgct | gccccagcct | agtcctggag | 660 |
| ccccaccttg | ggagaatgag | agtgtggtgc | gttaaatagg | cagcccagct | ggggacgtgc | 720 |
| ccagcatcca | ggcagggaag | ggtgggagag | ctcttggtct | gctgtattat | cacggagggg | 780 |
| tgcaggggggc | atgcagatca | ctctctcatg | agaacatcaa | caggggtcaga | ttagctctgc | 840 |
| agaggcttat | ggaggagcat | ggtggccaga | gatgggtcag | taccagagcc | cagggggggct | 900 |
| gaggccagga | catgcagaga | ggctggtgga | catagcagca | actctggttt | cttcttctcc | 960 |
| agtccatgtt | cataccctga | gggctaggca | tttgtaataa | caaacaaaca | agcaatttag | 1020 |
| aaatgggcca | ggcatggtgg | catgtgccta | tagtcccagc | tacttgggag | gccaaggcag | 1080 |
| gaggcctgct | tgaacccaga | aatttgaggc | cagcctgggc | aacacagcaa | gattatctta | 1140 |
| aaaaatttttt | tttaatctct | gagaaatggg | tagggccagg | aagtaaagga | tggccaaata | 1200 |
| ctccataagc | agcaaatgcg | tggctccaat | gtgaacaatg | atattataga | ctctgttctg | 1260 |
| agacctatgc | attgacacct | ccacctcccc | cactacatct | tgccaccta | aaaccactga | 1320 |
| gagtggtacc | tgctggaatg | ggtccacaca | cacagtcaca | catattttag | gcagggtagt | 1380 |
| tgacatcccc | agggaaaaag | agctcacaga | gagaggctga | atgttccaa | ctgggtagca | 1440 |
| gtaatagtac | atcatgctgt | acatggtaca | gcacagatca | ggtgaaaata | atagcacatc | 1500 |
| gtgattaacc | agggcttatt | ccagggagtc | aagaagagtt | tcatatcaga | aaaatctatc | 1560 |
| tttgtaattc | actataccag | taatcaaaga | aaaggattgt | acatttattt | tactagatgc | 1620 |
| agaaaatgaa | tttcataatt | gtcaacatct | actgatgata | aggaaaatgt | ataacaaaat | 1680 |
| aaagagacca | tttctgactt | gagaaaggat | aaataccaat | atgttatagc | aacagttctc | 1740 |
| aaactgttttt | ccagggaacc | ctaagaatcc | ctccttaggg | aggctttgat | ctcaaaatta | 1800 |
| tttttagaat | agtgctaaca | cactattttc | atgtttcagt | ctcatttttct | catgagtaca | 1860 |
| cacaatatga | caagttagtt | gatatgagtg | tggatttcca | catggtaact | gactttttcag | 1920 |
| aagctaccac | ttgttgagtt | tggtataata | tagaatagcc | acaattatct | aaaaatacca | 1980 |
| ttaaaataca | ctcccccatt | tcaactatat | atctgtgtga | ggctgaattt | tcttcatata | 2040 |
| ctccaaccta | aataacatat | taaaacaggt | tggatgatga | atcagatagg | aaaatccagc | 2100 |

```
tatgaaaaaa aaatcagaca tgaaaaattt tcaaaagggt aaaaccatag tactcttctt    2160
acttttttc ttttggaaga tggttatttt tcataaaaat atattattta tgttaacata     2220
tagaagatgg ataatttttt gaagaattga taaatgttta aattttttct ttctattatg    2280
gtaaatactg atgaatagag tccccataaa taaaagttct ttggggtatt caataatttt    2340
taatagtgta atgggatcct gagaccaaaa ggtttgagaa tcattgctct acagcaaaca    2400
ttatgtgtaa ttaagacact tcaggtgcat tctcaagaag accaataaag aggccacaat    2460
ggcaggcgtg gtggctcaca cttgtaatcc aagaacttag agaggacgag gcaggtggat    2520
cactggaggt caggaattct caaccagcct ggccaacatg tgaaaccct gtctctacta     2580
aaagtacaaa aattagtcgg gtgtagtggc aggtacctgt aatcccaagt acttgggggg    2640
ttgaggcagg agaatcactt gaagccggga ggtggaggct gcagtgagcc gagatcgtgc    2700
cactgcactc cagcctgggc aacggagtga gacttcatca tggaaaaaaa aacaaagagg    2760
ccaggatgtc tggttgttac tgccactgtt tcacatatcc ctgaaggacc tgcccaatgc    2820
taaagaaaca caaggaaggt aagaggtgaa agagaagaaa tgaaactatc attgtttgaa    2880
gatgacacca tcttttacat agaaaacctg ttagaatcaa atggcaagct attagaacta    2940
ctaagagaat tcagtgaggc tgctgtattc atggcaaaat tttaacaatt gatagcattt    3000
ctctgcaaca ttccttaata gttataaaat acagcacaaa gtagtaccaa aaatattaac    3060
tatctaggaa ataacctctt acagagaaaa tttagtctgt taaggataaa acagtggcaa    3120
tgtacgtcat gtccacagag attatatttt agcttagcaa agataccaat tctcccaaat    3180
ttatttataa attaaatgca atgtgaatca aaatttccca ctggaatttt tatcaggaag    3240
gcaacaaatt cttctttct ttctttcttt ctttctttat ttatttattt atttatttat    3300
ttatttattt ccttccttcc ttccttcctt ccttccttcc tttctttctt tctttctttc    3360
tttctttctt tctttctctc tctctttctc tctcccccc tctctctctc tctgtctctc    3420
tctctctctc tttctttctt tctttctttc tttcttttta agacaaagtc tggctctgtc    3480
acccaggctg cagtgcagtg atacaatctc agctcactga aacctcaacc tctccggcat    3540
caggtgaacc tcccacctca gcccccgag tagctgggac tacaggtgca caccactggg     3600
cctagataac ttttttgtatt tattgtaaat aaacacaaaa aataaatatt ttgctcaggt    3660
tggtctggaa ctcctgggct caagcaatcc gcctgccttg gcctcccaaa gtgctagaat    3720
tacagttgtg agccaccaca cccagccaat aaattaattc tttatgatga ataagttatc    3780
tatgaaaatt aagtcagctg ggtgcggtgg ctcacgcctg taatcccagc actttgccgg    3840
gctgaagcag gtggatcacc tgaggttggg agttcaagac cagccggacc aacatagaga    3900
aaacccgtct ctactaaaaa tgcaaaatta gctgggtgtg gtggcatatg cctgtaatcc    3960
cagatactta ggaggctgag gcaggagaat tgcttgaacc cgggcggtgg aggttgcggt    4020
gagccaagat tgcaccattg cactccagcc tgggccacaa gagcgaaact ccatctcaaa    4080
aaaaaaaaa gagaagttaa gtcaatgaaa agttaagtca attaaaaaag taagagctgt     4140
agtgtttaga tatatacaca cacacatata tatatattta tctttatata tgtatatata    4200
tcttttcctt ttttgagac cgagtctgtt tttgttgccc aggctggaat gcagtggcgc     4260
gatctctgct tactgcaacc tctgcctccc aggttcaagc gattctcgtg cctcagcctc    4320
ccgagtagct gggattacag gtgcctgccc catgcccgg ctaatttttg cattttagt      4380
agagacgggg tttcaccatg ttggccaggc tggtctcaaa ctcctgacct caggtgatcc    4440
accggcctca gcctcccaaa gtgctgggat tacaggtgtg agccaccgcg cccagccata    4500
```

```
tattttgctt tcatctgca gctcctggat cctaactcct tgttatattg ttgggcactt    4560
taggcctcag taaacagaat ctctgtctat gaccttctcc tgtccttctt ccacctgccc    4620
aaagcaggac tctaatttga ttgtgggtca aaagactctc attccagaaa gggccttgcc    4680
tcatacccta gaggaaggaa tgctgcacag aaacgccaag tctgaacaga caagccttgc    4740
tgggtttata ccatatgctt tttgtccaat cacatttctt catggttgcc aatcatgcct    4800
atgtaatgaa gcctccataa gaacccagaa ggacagggtt cagagagttt ccacatagct    4860
gaacactatc tggagagtga acacttccta gagagtggca cacccagaga gatcatgaaa    4920
gctccacgcc ccttcccct tacctcgccc tccacatctc ttcatctgta tctttcataa    4980
tatcctttat aaataaacca gcaaatgtgt ttccctgagt tatgtgagtc actctagcaa    5040
attaatcgaa cccaaagagg gggtcatggg aaccccaact tgaagccagt cagtcagaag    5100
ttccagaggc ccagacttgc aactggggag aaagagggg aggtcttggg gactgagccc    5160
ccaacctgtg ggatctgaca ctgtctccag gtaggtagtg ttggaactgc attggaggac    5220
actcctggtg tctgctgctt ggtgtgtggg gggaaaaacc cacacctttg gttacggagg    5280
tcttctgtgt tgacgatcat tgctgtttga gggcagaggg aatacacggt ttgagagagt    5340
ttttccctga catgagcgaa caggggacat gtactggtct ctgagatggg ggatcatggg    5400
atctgccaca agtggggaga ccactgtgac ccctgccaca gtctttgggg cagagggtgt    5460 ctcggggca gaagaagcga gagttgtttg cagtagcagt tatgtccaaa gtgggcgcca    5520
ggaaagtagg gctgcccagc tttgaagagc ctccttactc ccagcctgaa tgaaaccatt    5580
tcctgtaaag cgctaagcat aaagtttgcc aatggtgatc cacggagaag tgagtgtacc    5640
ccaccccgcc atcccacagg gaatgtcgga gtgatgttga tctgcaccta gggaaggaat    5700
ggttcatgag atgtggtgga gatgctgagg gcccgtggac atcagatcct accctacctg    5760
tgccaggaca agccatgcgc atgtgcttca gaccaccagg caacaggagt gttgcatgag    5820
gtgtgaagca ggcacctggg aaagaggagt gtgaacagca gatgggacac actgggggca    5880
gtcataggaa tgaaatgtcc caggatggat gcaggcaggt tatggaggac ttagtgagga    5940
ctgctctcct ggtgggaatt gtggagtggg agactggatg gagactggag gtgttttaag    6000
tagggaagcc aacttgcaag ggtgaccagg gaaactatgt cggccaaggg tgagacatgc    6060
actggcaaga ctctcagaca gcctggctta tctaagcaga atgcttgagc catgccaacg    6120
gtgcctcgca agttgtatta atcatgtcct ttcattttgt gtttttggtg cttggcatct    6180
gggcccttgc tgaccctaag ggaccatttc tctcagagct agtcaagtcc tagacacagt    6240
aaatgactct cctgggagca tgccttccat gtgcagacca accaatcaag agtccacact    6300
cccacccacc tcctttatcg agctctcaca tcctggggca ccatccacct gccctaatca    6360
ctcaaggacc acgtcccaaa caactaggga cagcctccat gccctgcac ccattgaaat    6420 tattcatgct agccaatcct aaacctgtgt atgctgccac accattcctt cctgcagaaa    6480
cacagtaagg actcttccta cacctcccct acttcctctg ctccctgact tacccactta    6540
cttcctggtg cagtcccctg tggcatagtt cactctcttc ttttgggaac tgtgaggcta    6600
tcttctcaat ggcagtcatc tcctgagctg ttggccttgc catacctaac taataataaa    6660
atctatattc taaggtaaaa acaaaacaga tagggtctca ctctgttgcc caggctggag    6720
tacagtggtg tgatcatgac tcactgcagc ctcaaactcc tgggctcaag cagttctctc    6780
atctcaacct cccgagtagc tgggactaca ggcacacacc accatgcctg gctagttttc    6840
```

```
ttatttttt  tgtagataca  gggtcttgtt  atgttgccaa  ggctggtctt  gaactcctgg    6900
gctcaagtga  tcctcctgcc  ttggcctccc  aaactgctgc  aattacaggc  atgagccacc    6960
atgcccagat  cagaaatctt  actaaaaata  tttcaaggag  aagagaaagc  caaagatgtt    7020
gaatatatat  atatgtgtgt  gtgtgtgtgt  gtatatatat  gtatatatgt  gtatatatgt    7080
gtgtatatat  atatgtatat  atgtatatat  atatgtatat  atgtatatat  atatgtatat    7140
tggggcaggc  gtggtggctc  atgcctgtgg  tcctaactac  ttgagagtct  gaggtgggag    7200
gattgcttga  gcctgggaga  tcgaggctgc  tgtgagctga  gactacacca  ctgcactcca    7260
gcttgggtga  cagagtgaga  ccctgtctcc  aaaaaaacaa  aaagaaaaag  aaaaaaagat    7320
ggaaaaagac  atgaaaaaac  aacaacagaa  atacccacac  atcatcaatg  ggagggaagc    7380
atcttgaggc  agcaaagcgg  gagtgctagt  agagaggcag  atagggcgtt  ggacctgagg    7440
cattaaggaa  agtcaggatt  tggagcttac  aagtctctca  ttggagatgg  gatggggttg    7500
gaatgaatgt  ctgagcaaac  acaaagcatt  tccttcccta  atgactcccc  accagtctaa    7560
agaatcccac  attaggtcga  acacggtggc  tcacgcctgt  aatcccagca  ctttgggagg    7620
ccaaggcggt  tggatcacga  ggtcaggaga  tcgagaccat  cttggctaac  atggtgaaac    7680
cccgtctcta  ctaaaaatac  aaaaaaatta  gccgggcgtc  atggtgggcg  cctgtagtcc    7740
cagctactcg  ggaggctgag  gcaggagaat  ggtgtgaacc  cgggaggcag  aacttgcagt    7800
gagcctagat  cgcgccactg  cactccagcc  tgggggacaa  aacgagactc  tgtctcaaaa    7860
aaaaaaaaaa  aaattcccac  attagagttg  gggaaatggg  cagtcctggt  ggaagttagg    7920
gaacagatct  gggacacgtt  atagccagct  ggactacagg  aggccataag  ctcaattctt    7980
ccttgactct  gaaaccttcc  actggtccta  atgcctagta  attccaggcc  tttcccagtt    8040
gtgccaggct  tggaggtgaa  cacatctatg  tgccaagaag  gaaaggtatg  ccaagcaggg    8100
gcttaagtca  tccttatcct  cagtctgtct  atgagtggta  tgtaccccctg  ttccccttgc    8160 aagatctgct  gggcttaggt  ctcctggctg  tgagttcccc  atacctgggc  ataaatgtag    8220
tgagcctgag  ctcccaaata  aggttggggg  ctccagagag  gtggagagcc  ctgtgtctgg    8280
gaagtgtgcc  cacccagcag  gtctgaccag  gaagatacac  tgctagggtt  atggaaaaag    8340
actatgtgtc  aaggtctctt  gattctccat  ctaggcagag  aatcatcttt  aattaatggg    8400
aaactggaag  gcaaattact  tggacctgaa  attacttttt  gtttattgaa  ccactgtgtt    8460
gtaaatcaca  tctctctgaa  ggcaagagaa  atcagggagt  tacaaaatgt  ttaggagaac    8520
taaacaggac  tccctgttttt  gctaactaat  cagattgaga  caggctctct  ggtaaatcta    8580
caaatttgat  gttgttcaac  cataagcagt  aaatttccta  tgctggattt  tcctgacaat    8640
gaatgtaaaa  ggaaaaggag  tcttttttgac  aaaaatatttt  attgttcatc  taaactgaaa    8700
aacttctcta  tttttcaaaa  ttgctatacg  tgtttaaaga  tgtagatatt  tgaatagcct    8760
aactggtaca  gaaggtttaa  tgatgattcc  taagacatac  ctataaatta  cttgaaattg    8820
aaacgaaatt  taagaagaat  tattggaatt  ttccccttct  caaatgagtt  cttagtttca    8880
taaatactat  acaagtccat  aagagatttg  ggttttgag  atgtctttt  ttttttttt    8940 ttttcagacg  gagtttcact  gttgttgcct  aggctggagt  gcaatggcgt  gacctcagct    9000
cactacaacc  tccacctccc  aggttcaagc  gattttcctg  cctcagcctc  ccaagtagct    9060
gggattacag  ggacctgcca  caacgccaag  ctaatgtttt  gtattttttag  tagagatggg    9120 gttcaccatg  ttggccaggc  ttgtctggaa  ctcctgacct  caggtgatcc  acccgcctat    9180
aatttattac  tccctttttgc  aaatgtttga  aaaggaataa  agtgcaatat  ttttaaacag    9240
```

```
aatgcagagt tctgttgtcc tttggcaata ccagtttcag actctgagag tggctcttgc     9300
tgttgccgac agtgggctga tgaccaaatc ccaacatgcc cccgctgcga gtccttcata     9360
acctgattca gtcatcactt agaggccagc aggcttcagg gaggcgtgag cctcagccaa     9420
caacctatag gggaagagac gcagaactca atgcagacag gtttggattc tggtgcctag     9480
agaatgcaac ttggaaactc tgagccagga gaaaagggtt ctctctccat gagagagtgt     9540
gggctttgtg agaagcgaca cacagcaaac acaattaaga gtccacccct cagcggggcg     9600
caggggctca cgcctgtaat cccagcactt tgggaggccg aggcgggtgg atcacgaggt     9660
caggagatca agaccatcct ggctaacaca gtgaaaccct gtctctacta aaaatacaaa     9720
aaaattagcc gggcgtggtg gcgggcgcct gtggtcccag ctactcggga ggctgaggca     9780
ggagaatggt gtgaacccgg gaggtggagc ttgcagtgag ccgagatcgc gccactgcac     9840
tccagcctgg gcgacagagc gagactccat ctcaaaaaaa aaaagaaaaa gaaaaagaaa     9900
aagagtccgc ccctgaatta aatagttggt ccttttgtgt tcctggtgat tcacttgcta     9960
agtggaagaa acaggaggga atcttttctc ctgccctcct g                        10001
```